United States Patent
Neumann

(10) Patent No.: US 12,374,439 B2
(45) Date of Patent: Jul. 29, 2025

(54) METHODS AND SYSTEMS FOR GENERATING A VIBRANT COMPATIBILITY PLAN USING ARTIFICIAL INTELLIGENCE

(71) Applicant: KPN INNOVATIONS, LLC., Lakewood, CO (US)

(72) Inventor: Kenneth Neumann, Lakewood, CO (US)

(73) Assignee: KPN INNOVATIONS LLC, Lakewood, CO (US)

(*) Notice: Subject to any disclaimer, the term of this patent is extended or adjusted under 35 U.S.C. 154(b) by 245 days.

(21) Appl. No.: 18/099,313

(22) Filed: Jan. 20, 2023

(65) Prior Publication Data
US 2023/0230673 A1 Jul. 20, 2023

Related U.S. Application Data

(63) Continuation-in-part of application No. 16/531,318, filed on Aug. 5, 2019, now Pat. No. 11,610,683.

(51) Int. Cl.
G06Q 30/00 (2023.01)
G16H 10/40 (2018.01)
G16H 20/60 (2018.01)

(52) U.S. Cl.
CPC ............. *G16H 20/60* (2018.01); *G16H 10/40* (2018.01)

(58) Field of Classification Search
None
See application file for complete search history.

(56) References Cited

U.S. PATENT DOCUMENTS

| | | | |
|---|---|---|---|
| 8,560,334 B2 | 10/2013 | Laehteenmaeki | |
| 10,127,361 B2 | 11/2018 | Hyde et al. | |
| 2005/0080650 A1 | 4/2005 | Noel | |
| 2007/0094090 A1 | 4/2007 | Jenkins | |
| 2009/0282296 A1* | 11/2009 | Lin | G05B 23/024 714/E11.029 |
| 2012/0225050 A1* | 9/2012 | Knight | A61K 38/4873 424/94.66 |

(Continued)

OTHER PUBLICATIONS

Knowing your genes: does this impact behaviour change? O'Donovan, Clare B; Walsh, Marianne C; Gibney, Michael J; Brennan, Lorraine; Gibney, Eileen R. The Proceedings of the Nutrition Society 76.3: 182-191. Cambridge: Cambridge University Press. (Aug. 2017). (Year: 2017).*

(Continued)

*Primary Examiner* — Matthew T Sittner
(74) *Attorney, Agent, or Firm* — Caldwell Intellectual Property Law

(57) ABSTRACT

An apparatus and method for optimizing nutrition and health, comprising at least a processor and a memory communicatively connected to the at least a processor, the memory containing instructions configuring the at least a processor to receive at least a biological extraction from a user, receive a discovery center experience score related to a user, retrieve a plurality of nutrient labels describing a plurality of nutrients, determine, as a function of the discovery center experience score and biological extraction, an importance factor of a nutrient of a plurality of nutrients and display the importance factor of a nutrient of a plurality of nutrients to a user.

18 Claims, 15 Drawing Sheets

(56) References Cited

U.S. PATENT DOCUMENTS

| | | | | |
|---|---|---|---|---|
| 2013/0022951 | A1* | 1/2013 | Hughes | G16H 20/60 |
| | | | | 434/262 |
| 2013/0304488 | A1 | 11/2013 | Girao et al. | |
| 2015/0278222 | A1* | 10/2015 | Claussenelias | G06F 16/953 |
| | | | | 707/723 |
| 2015/0363860 | A1 | 12/2015 | Lantrip et al. | |
| 2015/0371553 | A1 | 12/2015 | Vento | |
| 2016/0081632 | A1* | 3/2016 | Kamath | A61M 5/142 |
| | | | | 600/365 |
| 2016/0171514 | A1* | 6/2016 | Frank | G06Q 30/02 |
| | | | | 705/7.29 |
| 2016/0307128 | A1 | 10/2016 | Herman et al. | |
| 2017/0109475 | A1* | 4/2017 | Kaditz | G16H 50/80 |
| 2017/0135928 | A1* | 5/2017 | Giuliani | A61Q 5/02 |
| 2017/0199978 | A1* | 7/2017 | Landis | G16C 20/70 |
| 2018/0018767 | A1* | 1/2018 | Shih | G06T 7/11 |
| 2018/0122510 | A1* | 5/2018 | Apte | G16B 50/30 |
| 2018/0182479 | A1 | 6/2018 | Castellon et al. | |
| 2018/0189636 | A1 | 7/2018 | Chapela et al. | |
| 2018/0204274 | A1 | 7/2018 | Shimokawa et al. | |
| 2018/0233223 | A1* | 8/2018 | Solari | G16H 20/60 |
| 2018/0240542 | A1 | 8/2018 | Grimmer et al. | |

OTHER PUBLICATIONS

Assessment of Nutrient Intakes: Introduction to the Special Issue. Kirkpatrick, Sharon I; Collins, Clare E. Nutrients 8.4: 184. Basel: MDPI AG. (2016) (Year: 2016).*

Can metabotyping help deliver the promise of personalised nutrition? O'Donovan, Clare B; Walsh, Marianne C; Gibney, Michael J; Gibney, Eileen R; Brennan, Lorraine. The Proceedings of the Nutrition Society 75.1: 106-114. Cambridge: Cambridge University Press. (Feb. 2016) (Year: 2016).*

Nutritional label use, comprehension, and cardiovascular biomarkers in parents and youth Kakinami, Lisa; Houle, Stephanie; McGrath, Jennifer. Psychosomatic Medicine 76.3: A-51. Lippincott Williams and Wilkins. (Apr. 2014) (Year: 2014).*

Maldarelli, Calire; Popular Science, Oct. 25, 2016; A personalized nutrition company will use your DNA to tell you what to eat: https://www.popsci.com/personalized-nutrition-company-will-use-your-dna-to-tell-you-what-to-eat.

Polito, Lisa: Dec. 2, 2016; 3 companies expand the possibilities of personalized nutrition; https://www.newhope.com/products-and-trends/3-companies-expand-possibilities-personalized-nutrition.

Jones, Alexandra; Sep. 22, 2018; The Guardian; Blood, spit and swabs: can you trust home medical-testing kits?; https://www.theguardian.com/global/2018/sep/22/home-medical-testing-kits-blood-spit-swabs-trust-diy.

Habit Food Personalized; 2019; https://habit.com/how-it-works/.

Van Ommen, et al.; Nutrition Reviews vol. 75; Systems biology of personalized nutrition; https://watermark.silverchair.com/nux029.pdf?.

* cited by examiner

| Jerusalem Artichoke Table 700 | |
|---|---|
| Column 1 | Column 2 |
| Nutritional Biomarker 1 | Compatibility Index Value 1 |
| Nutritional Biomarker 2 | Compatibility Index Value 1 |
| Nutritional Biomarker 3 | Compatibility Index Value 2 |
| Nutritional Biomarker X | Compatibility Index Value 3 |
| Body Datum 1 | Compatibility Index Value 4 |
| Body Datum 2 | Compatibility Index Value 5 |
| Body Datum 3 | Compatibility Index Value 6 |
| Body Datum X | Compatibility Index Value 7 |
| Dietary State 1 | Compatibility Index Value 8 |
| Dietary State 2 | Compatibility Index Value 9 |
| Dietary Staate 3 | Compatibility Index Value 10 |
| Dietary State X | Compatibility Index Value 11 |
| Food Element 1 | Compatibility Index Value 12 |
| Food Element 2 | Compatibility Index Value 13 |
| Food Element 3 | Compatibility Index Value 14 |
| Food Element X | Compatibility Index Value 15 |

*FIG. 8*

METHODS AND SYSTEMS FOR GENERATING A VIBRANT COMPATIBILITY PLAN USING ARTIFICIAL INTELLIGENCE

This application is a continuation-in-part of U.S. Non-Provisional patent application Ser. No. 16/531,318, filed on Aug. 5, 2019, and entitled "METHODS AND SYSTEMS FOR GENERATING A VIBRANT COMPATIBILITY PLAN USING ARTIFICIAL INTELLIGENCE," the entirety of which is incorporated herein by reference.

FIELD OF THE INVENTION

The present invention generally relates to the field of artificial intelligence. In particular, the present invention is directed to methods and systems for generating a vibrant compatibility plan using artificial intelligence.

BACKGROUND

Accurate analysis of datasets can be challenging due to the vast amount of data to be analyzed. Incorrect analysis can lead to inaccuracies and frustrate users. Ensuring accurate selection and implementation is important.

SUMMARY OF THE DISCLOSURE

In an aspect, an apparatus for optimizing nutrition and health, including at least a processor and a memory communicatively connected to the at least a processor, the memory containing instructions configuring the at least a processor to receive at least a biological extraction from a user, receive a discovery center experience score related to a user, retrieve a plurality of nutrient labels describing a plurality of nutrients, determine, as a function of the discovery center experience score and biological extraction, an importance factor of a nutrient of a plurality of nutrients and display the importance factor of a nutrient of a plurality of nutrients to a user.

In an aspect, a method for optimizing nutrition and health, including receiving at least a biological extraction from a user, receiving a discovery center experience score related to a user, retrieving a plurality of nutrient labels describing a plurality of nutrients, determining, as a function of the discovery center experience score and biological extraction, an importance factor of a nutrient and displaying the importance factor of a nutrient of a plurality of nutrients to a user.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 8 is a block diagram illustrating an exemplary embodiment of a table contained within food element compatibility index value database;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a vibrant compatibility plan using artificial intelligence. In an embodiment, at least a server receives at least a composition datum from a user client device wherein the at least a composition datum includes at least an element of user body data and at least an element of desired dietary state data. In an embodiment, at least an element of user body data may include a nutritional biomarker such as a blood testing indicating the absence or presence of a particular gene. At least a server selects at least a correlated dataset containing a plurality of data entries wherein each dataset contains at least a datum of body data and at least a correlated compatible food element as a function of the at least a composition datum. For example, at least a server may select at least a dataset that contains body data that may match body data contained within at least a composition datum such as the same nutritional biomarker. At least a server creates at least an unsupervised machine-learning model wherein the at least an unsupervised machine-learning model further comprises generating a hierarchical clustering model to output at least a compatible food element as a function of the at least a composition datum and the at least a correlated dataset. At least a server generates at least a vibrant compatibility plan wherein the at least a vibrant compatibility plan further comprises a plurality of compatible food elements each containing at least a food element compatibility index value score as a function of the at least a hierarchical clustering.

Figure 1A:
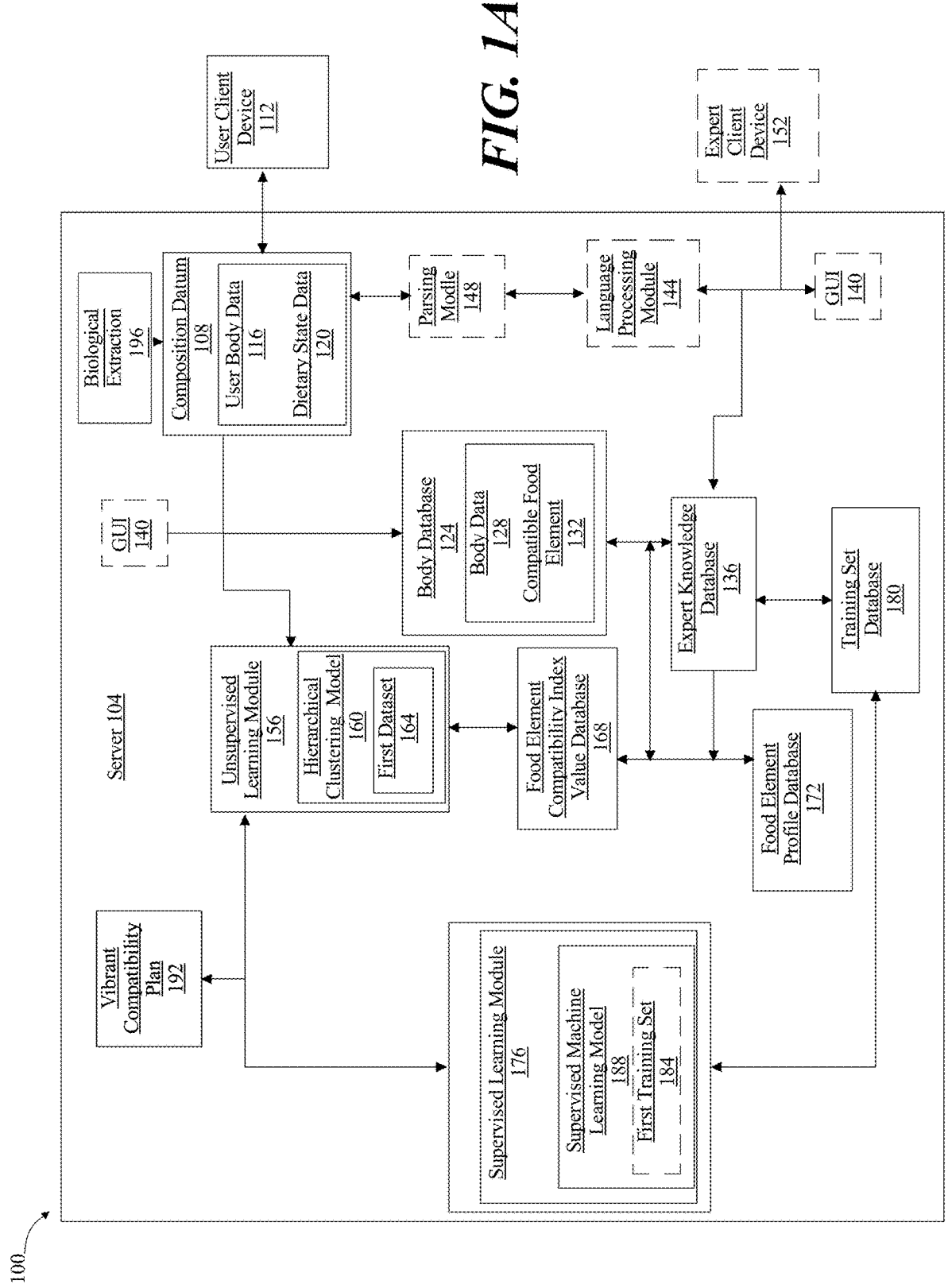
FIG. 1A is a block diagram illustrating an exemplary embodiment of a system for generating a vibrant compatibility plan using artificial intelligence.

Turning now to FIG. 1A, a system 100 for generating a vibrant compatibility plan using artificial intelligence is illustrated. System 100 includes at least a server 104. At least a server 104 may include any computing device as described herein, including without limitation a microcontroller, microprocessor, digital signal processor (DSP) and/or system on a chip (SoC) as described herein. At least a server 104 may be housed with, may be incorporated in, or may incorporate one or more sensors of at least a sensor. Computing device may include, be included in, and/or communicate with a mobile device such as a mobile telephone or smartphone. At least a server 104 may include a single computing device operating independently, or may include two or more computing device operating in concert, in parallel, sequentially or the like; two or more computing devices may be included together in a single computing device or in two or more computing devices. At least a server 104 with one or more additional devices as described below in further detail via a network interface device. Network interface device may be utilized for connecting a at least a server 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. At least a server 104 may include but is not limited to, for example, a at least a server 104 or cluster of computing devices in a first location and a second computing device or cluster of computing devices in a second location. At least a server 104 may include one or more computing devices dedicated to data storage, security, distribution of traffic for load balancing, and the like. At least a server 104 may distribute one or more computing tasks as described below across a plurality of computing devices of computing device, which may operate in parallel, in series, redundantly, or in any other manner used for distribution of tasks or memory between computing devices. At least a server 104 may be implemented using a "shared nothing" architecture in which data is cached at the worker, in an embodiment, this may enable scalability of system 100 and/or computing device.

With continued reference to FIG. 1, at least a server 104 is configured to receive at least a composition datum 108 from a user client device 112 generated as a function of at least a user conclusive label and at least a user dietary response, wherein the at least a composition datum further comprises at least an element of user body data and at least an element of desired dietary state data. Composition datum 108, as used herein, includes any data describing and/or relating to a nutritional state of a user. Nutritional state, as used herein includes the dietary requirements of a user and any associated nutrient levels, nutrient biomarkers, and/or biological samples obtained from a physically extracted sample of a user. Physically extracted sample, as used herein, includes a sample obtained by removing and analyzing tissue and/or fluid. Physically extracted sample may include without limitation a blood sample, a tissue sample, a buccal swab, a mucous sample, a stool sample, a hair sample, a fingernail sample, or the like. Physically extracted sample may include, as a non-limiting example, at least a blood sample. As a further non-limiting example, at least a biological extraction may include at least a genetic sample. At least a genetic sample may include a complete genome of a person or any portion thereof. At least a genetic sample may include a DNA sample and/or an RNA sample. At least a physically extracted sample may include an epigenetic sample, a proteomic sample, a tissue sample, a biopsy, and/or any other physically extracted sample. At least a biological extraction may include an endocrinal sample. In an embodiment, at least a biological extraction may be labeled to a category, such as a body system, and may be measured. As a further non-limiting example, the at least a biological extraction may include a signal from at least a sensor configured to detect physiological data of a user and recording the at least a biological extraction as a function of the signal. At least a sensor may include any sensor and/or device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. At least a sensor may include any electromagnetic sensor, including without limitation electroencephalographic sensors, magnetoencephalographic sensors, electrocardiographic sensors, electromyographic sensors, or the like. At least a sensor may include a temperature sensor. At least a sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. At least a sensor may detect any hematological parameter including blood oxygen level, pulse rate, heart rate, pulse rhythm, and/or blood pressure. At least a sensor may be a part of at least a server 104 or may be a part of a separate device in communication with at least a server 104.

With continued reference to FIG. 1A, nutritional state may include any data indicative of a person's nutritional biomarkers; nutritional state may be evaluated with regard to one or more measures of health of a person's body, one or more systems within a person's body such as a digestive system, a circulatory system, or the like, one or more organs within a person's body, one or more body dimensions of a person's body, and/or any other subdivision of a person's body useful for nutritional evaluation. Nutritional biomarkers may include, without limitation, one or more intracellular or extracellular measurements of vitamin levels such as Vitamin A, Vitamin B2, Vitamin D and the like. Nutritional biomarkers may include, without limitation, one or more intracellular or extracellular measurements of mineral levels such as calcium, magnesium, and iron. Nutritional biomarkers may include, without limitation, one or more intracellular or extracellular measurements of metabolites such as choline, inositol, and carnitine. Nutritional biomarkers may include, without limitation, one or more intracellular or extracellular measurements of electrolytes such as sodium and potassium. Nutritional biomarkers may include, without limitation, one or more intracellular or extracellular measurements of amino acids such as asparagine, glutamine, and serine. Nutritional biomarkers may include, without limitation, one or more intracellular or extracellular measurements of antioxidants such as Coenzyme Q10, cysteine, and glutathione. Nutritional biomarkers may include, without limitation, one or more intracellular or extracellular measurements of fatty acids and omega acids such as eicosatetraenoic acid (EPA), docosahexaenoic acid (DHA), and total omega 3 levels. Nutritional biomarkers may include, without limitation, one or more microbiome measurements such as stool tests that identify microorganisms living within a gut such as strains and/or quantities of bacteria, archaea, fungi, protozoa, algae, viruses, parasites, words, and the like. Nutritional biomarker may include, without limitation, one or more genetic measurements such as APOE gene that is involved in transportation of blood lipids such as cholesterol or MTHFR gene that is involved in making enzymes involved in metabolism and utilization of Vitamin B9 or FTO gene that is involved in a user's ability to feel full or satiated. Nutritional biomarker may include, without limitation, one or more gut wall measurements such as data describing on gut wall function, gut wall integrity, gut wall strength, gut wall absorption, gut wall permeability, intestinal absorption, gut wall absorption of bacteria. Gut wall measurements may include for example blood levels of creatinine levels or breath levels of lactulose, hydrogen, methane, lactose and the like. Nutritional biomarker may include one or more measurement of cognitive function, including any data generated using psychological, neuro-psychological and/or cognitive evaluations as well as diagnostic screening tests, personality tests, personal compatibly tests or the like.

With continued reference to FIG. 1A, composition datum 108 includes at least an element of user body data 116 and at least an element of desired dietary state data. User body data 116, as used herein, includes any nutritional biomarker, including any of the nutritional biomarkers as described above. For instance and without limitation, nutritional biomarker may include a salivary hormone panel that contains levels of estradiol, estrone, estriol, progesterone, testosterone, cortisol, and melatonin. In yet another non-limiting example, nutritional biomarker may include a blood sample result showing plasma levels of amino acids and metabolites utilized in folate metabolism and synthesis in the body. In yet another non-limiting example, nutritional biomarker may include a user self-reported previous diagnosis, medical condition, dietary elimination, self-diagnosis, dietary lifestyle, nutritional belief, nutritional habit and the like. For instance and without limitation, nutritional biomarker may include a user's self-reported gluten intolerance or a user's aversion to consume animal products. Nutritional biomarker may include a user's inability to consume a particular food or food group for religious reasons or an inability to consume a particular food or food group due to an immunoglobulin E (IGE) mediated response or an immunoglobulin G (IGG) mediated response. In yet another non-limiting example, nutritional biomarker may include a user's preference to consume certain foods or a user's self-described dietary elimination diet.

With continued reference to FIG. 1A, composition datum 108 includes at least an element of desired dietary state data. Desired dietary state data, as used herein, includes a user's goal eating habits and/or current eating habits. Eating habits as used herein, includes any data describing a user's food preferences, food allergies, food intolerances, style of eating, diet that a user may be following, meal types, and the like. Desired dietary state data 120 may include for example a user's goal to consume a gluten free diet or a diet free of artificial colors. Desired dietary state may be received as a function of a user conclusive label.

With continued reference to FIG. 1A, at least a composition datum is generated as a function of at least a user conclusive label and at least a user dietary response. User conclusive label as used herein, includes an element of data identifying and/or describing a current, incipient, or probable future medical condition affecting a person; medical condition may include a particular disease, one or more symptoms associated with a syndrome, a syndrome, and/or any other measure of current or future health and/or heathy aging. For example, user conclusive label may include an element of data indicating a diagnosis of a user from a medical professional such as for example, a diagnosis of celiac disease by a medical professional or a diagnosis of Vitamin C deficiency from a nutritionist. User conclusive label may be associated with a physical and/or somatic condition, a mental condition, a chronic infection, an immune disorder, a metabolic disorder, a connective tissue disorder, an excretory system disorder, a liver disorder, a joint disorder, a cancer, and the like. User conclusive label may be associated with a descriptor of latent, dormant, and/or apparent disorders, diseases, and/or conditions. User conclusive labels may include descriptors of conditions for which a person may have a higher than average probability of development such as a condition for which a person may have a "risk factor" such as for example a person suffering from abdominal obesity may have a higher than average probability of developing type II diabetes. In an embodiment, desired dietary state may be received as a function of a user conclusive label, such as for example when a medical professional may prescribe or desire a particular nutritional state linked to a user conclusive label. For instance and without limitation, a medical professional may prescribe a particular dietary state such as a vegan diet for a user with heart disease or a low carbohydrate diet for a user with a systemic *Candida albicans* infection. In yet another non-limiting example, a medical professional may prescribe a particular dietary state such as a diet rich in carbohydrates that contain B Vitamins for a user with alcoholism or a diet free of added sugars for a user with diabetes mellitus type 2.

With continued reference to FIG. 1A, at least an element of desired dietary state data may be received as a function of a user generated dietary response. User generated dietary response may include a user's own preference for a particular desired dietary state. For instance and without limitation, user may experience gas, bloating, diarrhea, and nausea after eating dairy containing foods such as milk, cheese, and ice cream. In such an instance, user may choose to eliminate such foods and generate a desired dietary state datum that includes a preference to consume a dairy free diet. In yet another non-limiting example, user may read in a magazine about a paleo diet being able to help individuals lose weight, whereby user may choose to follow a paleo diet. In such an instance, user may generate a desired dietary state datum that includes a preference to consume a paleo diet. In an embodiment, element of user body data 116 and element of desired dietary state data 120 may contain the same input. For example, element of user body data 116 may include a nutritional biomarker that contains a user self-reported elimination of food products containing nightshades and element of desired dietary state data 120 may contain an input containing a desire to follow a nightshade free diet. In an embodiment, user generated dietary response may be generated from a survey or questions that a user may answer. For example, user may respond to a series of prompted questions asking user about user's eating habits, user's eating preferences, foods that user routinely consumes and the like.

With continued reference to FIG. 1A, at least a server 104 receives at least a composition datum from a user client device generated as a function of at least a user conclusive label and at least a user dietary response. In an embodiment, user conclusive label such as a previous diagnosis of Multiple Sclerosis may be used to generate a desired dietary state that includes the Swank diet, and an element of user body data that includes a previously recorded magnetic resonance image (MRI). In an embodiment, user conclusive label may not contain a description, such as when a user has no known medical conditions or may not take any medications or supplements. In yet another non-limiting example, a user may utilize a previous diagnosis from childhood such as an anaphylactic response to tree nuts to generate a composition datum that includes a desired dietary state that does not contain tree nuts and an element of body data that contains symptoms of an anaphylactic reaction that a user experiences upon consumption of tree nuts and tree nut containing products such as rash, itchiness, hives, and throat swelling. In an embodiment, dietary response may be utilized to generate at least a composition datum. For example, a user may prefer to eliminate dairy products due to experiencing symptoms such as gas, bloating, and diarrhea after consuming dairy products. In such an instance, user may generate a composition datum that includes a body datum such as symptoms user experiences upon consuming dairy products and dietary state data that includes a diet free of dairy products. In yet another non-limiting example, a user may for example, perform a direct to consumer health test at home without the supervision of a medical professional that provides a user with results of a stool sample analysis containing an analysis of microbial species that may be present and/or absent within user's gastrointestinal tract. In such an instance, user may generate at least a composition datum containing body datum which includes stool sample analysis and at least a dietary response that may not select any one particular dietary state.

With continued reference to FIG. 1A, at least a server 104 is configured to receive at least a user conclusive label containing at least an incompatible food element as a function of at least a conclusive label neutralizer. Incompatible food element, as used herein, includes any food element that a user does not seek to consume. User may not consume a particular food element for religious reasons, ethical concerns, dislike of a particular food, an allergy to a particular food whether due to anaphylaxis, an intolerance, symptomology, and the like, and or any other reason that a user may not consume a particular food element. Incompatible food element may be generated as a function of at least a conclusive label neutralizer. Conclusive label neutralizer, as used herein, includes any process that may improve any physical condition identifiable in a conclusive label. Conclusive label neutralizer may include medications, supplements, nutrients, herbal remedies, exercise programs, medical procedures, physical therapies, psychological therapies, and the like. For example, conclusive label neutralizer may include a specific medication designed to treat a user's nail fungus or conclusive label neutralizer may include a particular supplement utilized to balance out a user's symptoms of estrogen dominance. User conclusive label may be generated as a function of a conclusive label neutralizer, such as when a certain medication, supplement, and/or medical procedure may be associated with incompatible food elements. For example, a conclusive label neutralizer such as a statin medication that is utilized to reduce total cholesterol levels may be utilized to generate an incompatible food element that includes grapefruit and grapefruit containing food products. In yet another non-limiting example, a conclusive label neutralizer such as doxycycline for acne may be utilized to generate an incompatible food element that includes dairy products. In yet another non-limiting example, a conclusive label neutralizer such as high-intensity training may be utilized to generate an incompatible food element such as grain products as part of a paleo-centered approach often coupled with high-intensity training.

With continued reference to FIG. 1A, at least a server 104 is designed and configured to receive at least a user dietary response containing at least an acute vibrancy input, at least a chronic vibrancy input, and at least a longevity vibrancy input. Acute vibrancy input, as used herein, includes any short-term dietary response. For example, acute vibrancy input may include elimination of certain food elements such as cookies, donuts, and cakes because of an upcoming wedding or event such as a graduation. In yet another non-limiting example, acute vibrancy input may include a desire to eliminate all carbohydrates from one's diet for three months before a spring break trip to Mexico. Chronic vibrancy input, as used herein, includes any chronic dietary response. For example, chronic vibrancy input may include elimination of certain food elements as part of an ongoing health plan or health goal. For example, a chronic vibrancy input may include a chronic elimination of food elements such as sugar due to an ongoing health plan to lose weight. In yet another non-limiting example, a chronic vibrancy input may include a chronic elimination of nightshades food elements such as tomatoes and eggplant as part of an ongoing elimination diet. Longevity vibrancy input, as used herein, includes any lifelong dietary response. For example, longevity vibrancy input may include a permanent elimination of simple carbohydrates for a user with a chronic medical condition such as diabetes. In yet another non-limiting example, longevity vibrancy input may include elimination of food elements high in saturated fat such as coconut and shrimp for a user with heart disease.

With continued reference to FIG. 1A, a user client device 112 may include, without limitation, a display in communication with at least a server 104; display may include any display as described herein. A user client device 112 may include an additional computing device, such as a mobile device, laptop, desktop computer, or the like; as a non-limiting example, the user client device 112 may be a computer and/or workstation operated by a medical professional. Output may be displayed on at least a user client device 112 using an output graphical user interface 140, as described in more detail below. Transmission to a user client device 112 may include any of the transmission methodologies as described herein.

With continued reference to FIG. 1A, at least a server 104 is configured to select at least a correlated dataset containing a plurality of data entries wherein each dataset contains at least a datum of body data and at least a correlated compatible food element as a function of the at least a composition datum 108. Body data, as used herein, includes any of the data suitable for use as user body data 116 as described above. For instance, and without limitation, body data may include blood results showing particular extracellular levels of nutrients such as Vitamin D, Vitamin K, and Vitamin E. In yet another non-limiting example, body data may include stool results showing particular biomarkers within a gastrointestinal tract such as for example, beneficial short-chain fatty acids (SCFA) with n-butyrate, fecal lactoferrin, beneficial bacteria, additional bacteria and the like. In yet another non-limiting example, body data may include a particular diet or way of eating such as for example a macrobiotic diet or a low FODMAP diet. Datasets may be selected and contained within body database 124 as described below in more detail in reference to FIG. 2.

With continued reference to FIG. 1A, each dataset contains at least a datum of body data 128 and at least a correlated compatible food element 132. Compatible food element as used herein, includes any element of data identifying and/or describing any food substance that a user may consume as a function of a datum of body data. Food substance, as used herein, includes any substance consumed to provide nutritional support for an organism such as a human being. Food substance may include for example, a particular food such as kale, cabbage, and chicken. Food substance may include a category of food that may be categorized as having a shared characteristic or trait. For example, food substance may include categories such as dairy products, vegetables, animal proteins, seafood, fats, carbohydrates, and the like. In an embodiment, at least a datum of body data is correlated with a compatible food element where the element of body data is located in the same data element and/or portion of data element as the body data; for example, and without limitation, an element of body data is correlated with a compatible food element where both element of body data and compatible food element are contained within the same first dataset 164 or are both collected from the same user. For instance and without limitation, body data showing an overgrowth of yeast in a user's gastrointestinal tract may be correlated to a compatible food element such as garlic which is shown to be effective in killing *Candida albicans*. In yet another non-limiting example, body data showing low salivary levels of progesterone may be correlated to a compatible food element such as pumpkin, sweet potato, and broccoli.

With continued reference to FIG. 1A, dataset containing plurality of data entries wherein each dataset contains at least a datum of body data and at least a correlated compatible food element may be stored in a body database as described below in more detail in reference to FIG. 2. Dataset may be stored in any suitable data and/or data type. For instance and without limitation, dataset may include textual data, such as numerical, character, and/or string data. Textual data may include a standardized name and/or code for a disease, disorder, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used as dataset may take; persons skilled in the art, upon reviewing the entirety of this disclosure, will be aware of various forms which may be suitable for use as dataset consistently with this disclosure.

With continued reference to FIG. 1A, dataset may be stored as image data, such as for example an image of a particular food substance such as a photograph of a pear or an image of a steak. Image data may be stored in various forms including for example, joint photographic experts group (JPEG), exchangeable image file format (Exif), tagged image file format (TIFF), graphics interchange format (GIF), portable network graphics (PNG), netpbm format, portable bitmap (PBM), portable any map (PNM), high efficiency image file format (HEIF), still picture interchange file format (SPIFF), better portable graphics (BPG), drawn filed, enhanced compression wavelet (ECW), flexible image transport system (FITS), free lossless image format (FLIF), graphics environment manage (GEM), portable arbitrary map (PAM), personal computer exchange (PCX), progressive graphics file (PGF), gerber formats, 2 dimensional vector formats, 3 dimensional vector formats, compound formats including both pixel and vector data such as encapsulated postscript (EPS), portable document format (PDF), and stereo formats.

With continued reference to FIG. 1A, datasets contained within body database may be obtained from a plurality of sources. Datasets contained within body database may contain a plurality of data entries, obtained for example, from patient medical records that have been stripped of identifying information. Datasets contained within body database may be obtained from patient surveys who may be sampled in a variety of methods such as by phone, mail, internet and the like. Patient surveys may be distributed to patients across a breadth of geographical locations and may also be stripped of identifying information. Datasets contained within body database may be obtained from clinical data such as from facilities including nursing homes, hospitals, home health agencies, and the like as described below in more detail in reference to FIG. 6.

With continued reference to FIG. 1A, datasets contained within body database may be obtained from an expert knowledge database. Expert knowledge database 136 may include data entries reflecting one or more expert submissions of data such as may have been submitted according to any process, including without limitation by using graphical user interface 140. Information contained within expert knowledge database 136 may be received from input from expert client device. Expert client device may include any device suitable for use as user client device 112 as described above. Expert knowledge database 136 may include one or more fields generated by a language processing module, such as without limitation fields extracted from one or more documents such as for example medical journals, scientific journals, medical articles, scientific articles, medical reviews, scientific reviews, medical trials, scientific trials and the like. Documents may be stored and/or retrieved by at least a server 104 and/or language processing module 144 in and/or from a document database. Documents in document database may be linked to and/or retrieved using document identifiers such as URI and/or URL data, citation data, or the like; persons skilled in the art, upon reviewing the entirety of this disclosure, will be aware of various ways in which documents may be indexed and retrieved according to citation, subject matter, author, data, or the like as consistent with this disclosure.

With continued reference to FIG. 1A, at least a server 104 may receive a list of significant categories of body data and/or compatible food elements from at least an expert. In an embodiment, at least a server 104 may provide a graphical user interface 140, which may include without limitation a form or other graphical element having data entry fields, wherein one or more experts, including without limitation clinical and/or scientific experts, may enter information describing one or more categories of body data that the experts consider to be significant or useful for detection of conditions; fields in graphical user interface 140 may provide options describing previously identified categories, which may include a comprehensive or near-comprehensive list of types of user input datums detectable using known or recorded testing methods, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface 140 or the like may include fields corresponding to correlated compatible food elements, where experts may enter data describing compatible foods the experts consider related to entered categories of body data; for instance, such fields may include drop-down lists or other pre-populated data entry fields listing currently recorded body data, and which may be comprehensive, permitting each expert to select a compatible food element the expert believes to be predicted and/or associated with each category of body data selected by the expert. Fields for entry of body data and/or compatible food elements may include free-form data entry fields such as text entry fields; as described above, examiners may enter data not presented in pre-populated data fields in the free-form data entry fields. Alternatively or additionally, fields for entry of body data and/or compatible food elements may enable an expert to select and/or enter information describing or linked to a category of body data that the expert considers significant, where significance may indicate likely impact on longevity, mortality, quality of life, or the like as described in further detail below. Graphical user interface 140 may provide an expert with a field in which to indicate a reference to a document describing significant categories of body data, relationships of such categories to compatible food elements, and/or significant categories of compatible food elements. Any data described above may alternatively or additionally be received from experts similarly organized in paper form, which may be captured and entered into data in a similar way, or in a textual form such as a portable document file (PDF) with examiner entries, or the like.

With continued reference to FIG. 1A, data information describing significant categories of body data, relationships of such categories to compatible food element may be extracted from one or more documents using a language processing module 144. Language processing module 144 may include any hardware and/or software module. Language processing module 144 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model Still referring to FIG. 1A, language processing module 144 may compare extracted words to categories of body data recorded by at least a server 104, and/or one or more categories of compatible food substances recorded by at least a server 104; such data for comparison may be entered on at least a server 104 as using expert data inputs or the like. In an embodiment, one or more categories may be enumerated, to find total count of mentions in such documents. Alternatively or additionally, language processing module 144 may operate to produce a language processing model. Language processing model may include a program automatically generated by at least a server 104 and/or language processing module 144 to produce associations between one or more words extracted from at least a document and detect associations, including without limitation mathematical associations, between such words, and/or associations of extracted words with categories of user input datums, relationships of such categories to first probing elements, and/or categories of first probing elements. Associations between language elements, where language elements include for purposes herein extracted words, categories of user input datums, relationships of such categories to first probing elements, and/or categories of first probing elements may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of user input datum, a given relationship of such categories to a first probing element, and/or a given category of a first probing element. As a further example, statistical correlations and/or mathematical associations may include probabilistic formulas or relationships indicating a positive and/or negative association between at least an extracted word and/or a given category of body data, a given relationship of such categories to compatible food element, and/or a given category of compatible food element; positive or negative indication may include an indication that a given document is or is not indicating a category of body data, relationship of such category to a first compatible food element, and/or category of compatible food elements is or is not significant. For instance, and without limitation, a negative indication may be determined from a phrase such as "High stool fungal overgrowth was not found to be compatible with high fructose corn syrup" whereas a positive indication may be determined from a phrase such as "Low serum sodium levels was found to be compatible with sea salt" as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory by at least a server 104, or the like.

Still referring to FIG. 1A, language processing module 144 and/or at least a server 104 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein, are statistical models with inference algorithms that that may be applied to the models. In such models, a hidden state to be estimated may include an association between an extracted word category of body data, a given relationship of such categories to compatible food element, and/or a given category of compatible food elements. There may be a finite number of category of body data a given relationship of such categories to a compatible food element, and/or a given category of food elements to which an extracted word may pertain; an 1-MM inference algorithm, such as the forward-backward algorithm or the Viterbi algorithm, may be used to estimate the most likely discrete state given a word or sequence of words. Language processing module 144 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1A, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1A, language processing module 144 may use a corpus of documents to generate associations between language elements in a language processing module 144 and at least a server 104 may then use such associations to analyze words extracted from one or more documents and determine that the one or more documents indicate significance of a category of body data, a given relationship of such categories to compatible food elements, and/or a given category of food elements. In an embodiment, at least a server 104 may perform this analysis using a selected set of significant documents, such as documents identified by one or more experts as representing good science, good clinical analysis, or the like; experts may identify or enter such documents via graphical user interface 140, or may communicate identities of significant documents according to any other suitable method of electronic communication, or by providing such identity to other persons who may enter such identifications into at least a server 104. Documents may be entered into at least a server 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, at least a server 104 may automatically obtain the document using such an identifier, for instance by submitting a request to a database or compendium of documents such as JSTOR as provided by Ithaka Harbors, Inc. of New York.

With continued reference to FIG. 1A, at least a server may be configured to extract at least a physiological trait from at least a composition datum 108 and match the at least a physiological treat to at least a correlated dataset containing at least an element of the at least a physiological trait. Physiological trait, as used herein, includes information, data, and/or description relating a functioning of a user's body. Physiological trait may include any data suitable for use as body data as described above, including for example any nutritional biomarker. For example, physiological data may include a measured blood value of a nutrient such as zinc, a stool test reflecting a bacterial count, bacterial species, and the like. Physiological trait may include a nutritional biomarker such as a mutation of the congenital lactase deficiency gene or a mutation of TCF7L2 gene that regulates insulin secretion.

With continued reference to FIG. 1A physiological trait may be extracted from a composition datum 108 by a parsing module 148 operating on at least a server 104. Parsing module 148 may parse at least a composition datum 108 for at least a physiological trait and match the at least a physiological trait to at least a correlated dataset containing at least an element of the at least a physiological trait. In an embodiment, datasets contained within body database may be categorized by physiological traits, as described in more detail below in reference to FIG. 2. Parsing module 148 may match at least a dataset by extracting one or more keywords containing words, phrases, test results, numerical scores, and the like from composition datum 108 and analyze the one or more keywords utilizing for example, language processing module 144 as described in more detail below. Parsing module 148 may be configured to normalize one or more words or phrases of user input, where normalization signifies a process whereby one or more words or phrases are modified to match corrected or canonical forms; for instance, misspelled words may be modified to correctly spelled versions, words with alternative spellings may be converted to spellings adhering to a selected standard, such as American or British spellings, capitalizations and apostrophes may be corrected, and the like; this may be performed by reference to one or more "dictionary" data structures listing correct spellings and/or common misspellings and/or alternative spellings, or the like. Parsing module 148 may perform algorithms and calculations when analyzing tissue sample analysis and numerical test results. For instance and without limitation, parsing module 148 may perform algorithms that may compare test results contained within composition datum 108, tissue analysis results, and/or biomarker levels to normal reference ranges or values. For example, parsing module 148 may perform calculations that determine how many standard deviations from normal levels a salvia hormone test containing salivary levels of progesterone are from normal reference ranges. In yet another non-limiting example, parsing module 148 may perform calculations between different values contained within composition datum 108. For example, parsing module 148 may calculate a ratio of progesterone to estradiol levels from a blood test containing a hormone panel that may include progesterone, estradiol, estrone, estriol, and testosterone serum levels.

With continued reference to FIG. 1A, parsing module 148 may extract and/or analyze one or more words or phrases by performing dependency parsing processes; a dependency parsing process may be a process whereby parsing module 148 recognizes a sentence or clause and assigns a syntactic structure to the sentence or clause. Dependency parsing may include searching for or detecting syntactic elements such as subjects, objects, predicates or other verb-based syntactic structures, common phrases, nouns, adverbs, adjectives, and the like; such detected syntactic structures may be related to each other using a data structure and/or arrangement of data corresponding, as a non-limiting example, to a sentence diagram, parse tree, or similar representation of syntactic structure. Parsing module 148 may be configured, as part of dependency parsing, to generate a plurality of representations of syntactic structure, such as a plurality of parse trees, and select a correct representation from the plurality; this may be performed, without limitation, by use of syntactic disambiguation parsing algorithms such as, without limitation, Cocke-Kasami-Younger (CKY), Earley algorithm or Chart parsing algorithms. Disambiguation may alternatively or additionally be performed by comparison to representations of syntactic structures of similar phrases as detected using vector similarity, by reference to machine-learning algorithms and/or modules.

With continued reference to FIG. 1A, parsing module 148 may combine separately analyzed elements from composition datum 108 to extract and combine at least a keyword. For example, a first test result or biomarker reading may be combined with a second test result or biomarker reading that may be generally analyzed and interpreted together. For instance and without limitation, a nutritional biomarker of zinc may be reading and analyzed in combination with a nutritional biomarker reading of copper as excess zinc levels can deplete copper levels. In such an instance, parsing module 148 may combine nutrition biomarker reading off zinc and biomarker reading of copper and combine both levels to create one keyword. In an embodiment, combinations of tissue sample analysis, keywords, or test results that may be interpreted together may be received from input received from experts and may be stored in an expert knowledge database. Expert client device 152 may include any device suitable for use as user client device 112 as described above.

With continued reference to FIG. 1A, at least a server 104 may include an unsupervised machine-learning module 156 operating on at least a server and/or on another computing device in communication with at least a server 104, which may include any hardware or software module. At least a server is configured to create at least an unsupervised machine learning model wherein the at least an unsupervised machine learning model further comprises a hierarchical clustering model 160 to output at least a compatible food element as a function of the at least a composition datum 108 and the at least a correlated dataset. An unsupervised machine-learning process, as used herein, is a process that derives inferences in datasets without regard to labels; as a result, an unsupervised machine-learning process may be free to discover any structure, relationship, and/or correlation provided in the data. For instance, and without limitation, unsupervised machine learning module and/or at least a server 104 may perform an unsupervised machine learning process on a first data set, which may cluster data of first data set according to detected relationships between elements of the first data set, including without limitation correlations of elements of body data to each other and correlations of compatible food element to each other; such relations may then be combined with supervised machine learning results to add new criteria for at supervised machine-learning processes as described in more detail below. As a non-limiting, illustrative example, an unsupervised process may determine that a first body datum correlates closely with a second body datum, where the first element has been linked via supervised learning processes to a given compatible food element, but the second has not; for instance, the second body datum may not have been defined as an input for the supervised learning process, or may pertain to a domain outside of a domain limitation for the supervised learning process. Continuing the example a close correlation between first body datum and second body datum may indicate that the second body datum is also a good predictor for the compatible food element; second body datum may be included in a new supervised process to derive a relationship or may be used as a synonym or proxy for the first body datum.

With continued reference to FIG. 1A, hierarchical clustering model 160 may include any method of cluster analysis which outputs a hierarchy of clusters. Cluster analysis, as used herein, includes any grouping of objects such as datasets in such a way that datasets in the same group or cluster are more similar to each other than to those in other clusters. Cluster analysis may include hard clustering and/or soft clustering. Hard clustering may include clustering where each dataset belongs to any particular cluster or not. Soft clustering may include clustering where each dataset may belong to a cluster to a certain degree such as a certain percentage of belonging to any given cluster or a likelihood of belonging to a given cluster. Hierarchical clustering may group and/or segment datasets with shared attributes to extrapolate algorithmic relationships. Hierarchical clustering model 160 may include generating various algorithms that may work to find clusters that may be generated based on parameter settings such as distance functions to use, density threshold, and optimal of clusters to generate. Hierarchical clustering model 160 may include models such as but not limited to connectivity models, centroid models, distribution models, density models, subspace models, group models, graph-based models, signed graph models, neural models, and the like.

With continued reference to FIG. 1A, hierarchical clustering model 160 may include agglomerative and/or divisive hierarchical clustering. Agglomerative hierarchical clustering may include a bottom-up approach whereby each observation may start in its own cluster, and pairs of clusters may be merged as one moves up the hierarchy. Divisive hierarchical clustering may include a top-down approach whereby all observations may start in one cluster and splits may be performed recursively moving down the hierarchy.

With continued reference to FIG. 1A, at least a server 104 may be configured to retrieve at least a food element compatibility index value correlated to at least a food element from a database and rank the at least a food element as a function of the food compatibility index. Food element compatibility index value, as used herein, is a value assigned to a food element indicating a degree of compatibility between a food element any given element of food data. Food compatibility index value may be stored in a food compatibility index value database operating on at least a server 104. A given food element may contain a plurality of index values each correlated to an element of body data. For example, a food element may contain a first index value correlated to a first element of body data and the same food element may contain a second index value correlated to a second element of body data. Food element compatibility index value may be based on a numerical score whereby a high numerical value may indicate a high degree of compatibility whereby a low numerical value may indicate a low degree of compatibility. Food element compatibility index values may vary for any single variant of any particular body data. For instance and without limitation, a food element such as brie cheese may be correlated to a low food element compatibility index value for a first element of body data that shows a G/G genotype of the MCM6 gene that controls production of lactase enzyme and thereby indicates an inability to produce lactase efficiently with the G/G genotype, whereby brie cheese may be correlated to a higher food element compatibility index value for a second element of body data that shows an A/A genotype of the MCM6 gene that indicates an ability to produce lactase efficiently. In an embodiment, food element compatibility index value may include a score relating compatibility between a first food element and a second food element for any given body datum. For example, food element compatibility index value may include a value that reflects the ability for a user with a body datum such as a G/G genotype of the FUT2 gene that controls enzyme production to absorb Vitamin B12 in the digestive tract, to consume a second compatible food element such as lamb based on a high compatibility score for a first food element such as pork. In such an instance, food element compatibility index value may reflect ability to substitute a first compatible food element for a second compatible food element and/or ability to consume a second compatible food element as a function of being able to consume a first compatible food element for a user with a given user body datum. In an embodiment, at least a server 104 may rank compatibility of at least a food element as a function of the at least a food compatibility index value. For instance, a food element with a high food compatibility index value may be ranked highly compatibly for a user as compared to a food element with a low food compatibility index value. In an embodiment, ranking at least a food element may include a hierarchical ranking that may rank food elements in decreasing and/or increasing level of compatibility.

With continued reference to FIG. 1A, food element compatibility index value may be calculated as a function of at least a composition datum 108 and a first food element profile. First food element profile may include information describing a nutrient density score of a food element correlated to a given composition datum 108. Nutrient density may include a ranking and/or score reflecting the amount and/or quantity of vitamins, minerals, electrolytes, amino acids, antioxidants, micronutrients, fatty acids, and the like contained within a given food element and may be stored in a food element profile database 172 as described below in more detail in reference to FIG. 9. For example, an apple may have a high nutrient density score due to the Vitamin C, fiber, calcium, iron, Vitamin A, polyphenols, antioxidants and potassium contained with an apple as compared to a hot dog which may have a lower nutrient density score due to the presence of nitrates, excess sodium and sugar. In an embodiment, nutrient density scores may contain numerical values that may indicate the nutrient density of any given food element. In an embodiment, a high numerical nutrient density score may indicate a high amount of nutrients contained within a particular food element as compared to a low numerical nutrient density score which may indicate a low amount of nutrients contained within a particular food element. In an embodiment, nutrient density scores may be contained within a database operating on at least a server. In an embodiment, nutrient density scores may be calculated taking into account for example, absence of certain nutrients known to be beneficial such as vitamins and antioxidants as well as presence of certain nutrients that may not be as beneficial such as nitrates, preservatives and artificial ingredients for example.

With continued reference to FIG. 1A, system 100 may include a supervised machine-learning module 176 operating on at least a server 104. Supervised machine-learning module 176 may select a training set from training set database 180 as described below in more detail in reference to FIG. 11. Supervised module is configured to select at least a first training set 184, create at least a supervised machine learning model 188 using the at least a first training set 184 wherein the at least a supervised machine learning model 188 relates body data to compatible food elements and generate at least a compatible food element as a function of the at least a composition datum 108 and the at least a first training set 184.

With continued reference to FIG. 1A, at least a server 104 may select at least a training set from training set database 180. Training set database 180 may contain training sets pertaining to different categories and classification of information, including training set components which may contain sub-categories of different training sets. In an embodiment, at least a server may select at least a first training set 184 by categorizing at least a composition datum 108 to contain at least a physiological label and select at least a first training set 184 as a function of the at least a physiological label. Physiological label, as used herein, includes any categorization and/or classification of a user body datum as belonging to a particular physiological categorization describing a user body datum as belonging to a particular body system. For example and without limitation, body system may include body dimensions which include classification by particular root cause pillars of disease. Dimension of the human body may include epigenetics, gut wall, microbiome, nutrients, genetics, and metabolism. In an embodiment, training set database 180 may contain training sets classified to body dimensions. In such an instance, training sets may be classified to more than one body dimension. For instance and without limitation, a training set may be classified to gut wall and microbiome. In yet another non-limiting example, a training set may be classified to nutrients and metabolism. First training set 184 may be selected by matching physiological label to a training set containing a matching physiological label. For example, a physiological label that contains microbiome may be matched to a training set containing a physiological label that contains microbiome. In an embodiment, first training set 184 may include the at least a correlated dataset.

With continued reference to FIG. 1A, supervised machine learning model 188 may include without limitation model developed using linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Supervised machine-learning algorithms may include without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors' algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

With continued reference to FIG. 1A, supervised machine-learning algorithms may include using alternatively or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using any training set as described herein; the trained network may then be used to apply detected relationships between elements of user input datums and antidotes.

Training data, as used herein, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1A, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name and/or a description of a medical condition or therapy may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below.

Figure 1B:
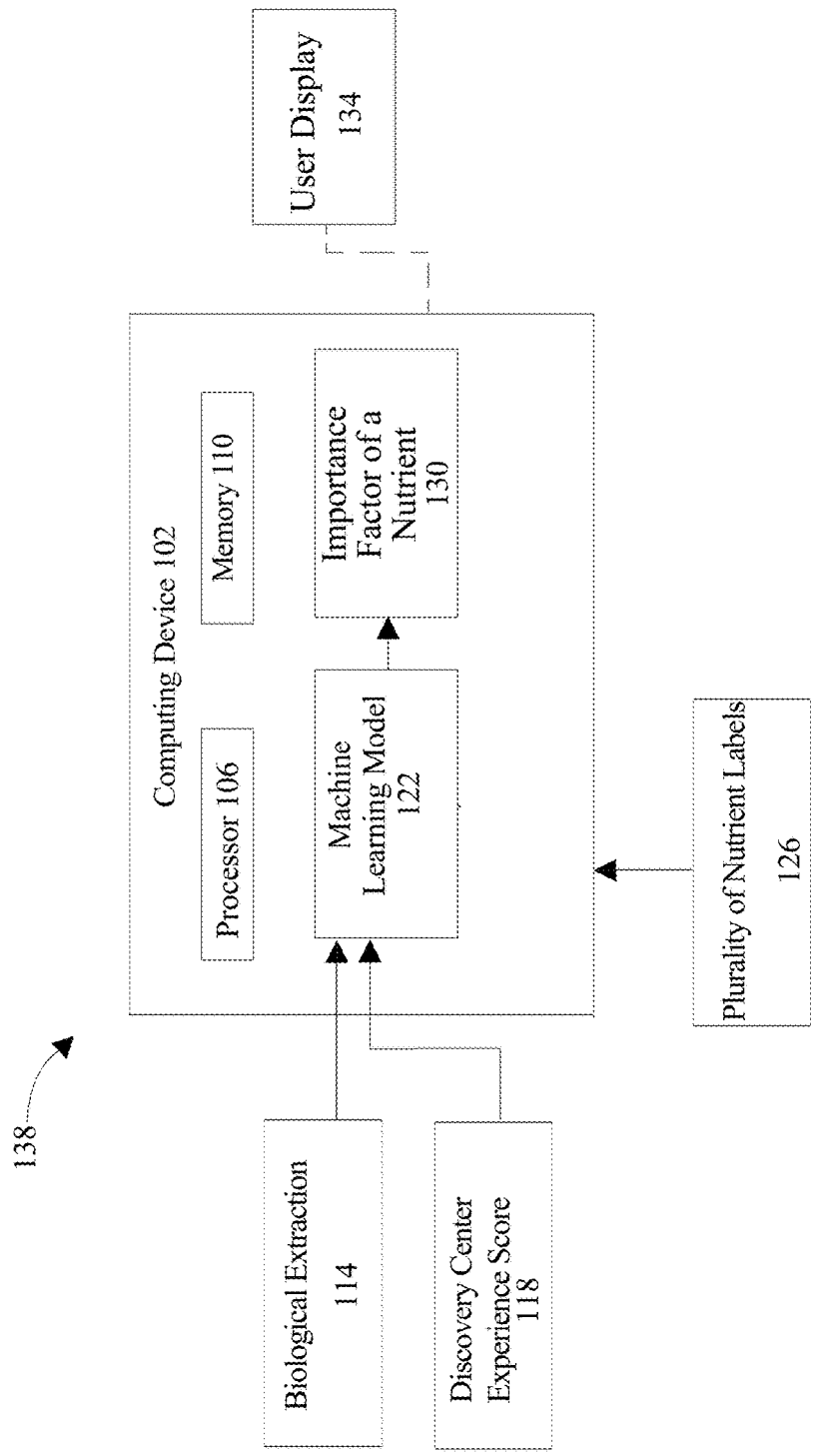
FIG. 1B is a block diagram illustrating an exemplary embodiment of an apparatus for optimizing nutrition and health.

Referring now to FIG. 1B, apparatus 138 may be configured to extract information from a discovery center experience. "Discovery center experience" as used in this disclosure is defined as a set of simulated data generated at an online platform, known as a discovery center, which describes various potential health experiences to optimize user's health. "Simulated data" as used in this disclosure is defined as taking a large amount of data and using it to mimic real-world scenarios of conditions. For example, a discovery center experience may include a future user experience wherein a comprehensive body scan may be performed, and user may be portrayed in a 3 dimensional version and have an experience to simulate what happens if user chooses optimal nourishment. User may also see what their future self may look like 3, 6, 9 or 12 months into the future and the like. A user display may show what living optimally looks like as well as what user could look like with no change and alternatively, what user could look like without proper nourishment. "A Discovery Center Experience" as used in this disclosure may also include one or a number of biological extractions from the user. These biological extractions might include physical experiences, diagnostic testing, sleep patterns, fitness patterns, current nutrient levels or any other form of information coming from the user that is then utilized to determine their optimal nourishment needs. Nourishment needs include a complete state of physical, mental, nutritional, and spiritual wellbeing.

A "biological extraction" as used in this disclosure, includes any element of physiological state data. Physiological data may include any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss.

With continued reference to FIG. 1, physiological data may be obtained from a physical sample. A "physical sample" as used in this example, may include any sample obtained from a human body of a user. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with a human body of a user such as a microchip embedded in a user's skin, a sensor in contact with a user's skin, a sensor located on a user's tooth, and the like.

Continuing to refer to FIG. 1, biological extraction contains a plurality of user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS) Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, blood clotting factors, With continued reference to FIG. 1, gut-wall body measurement may include one or more stool test results describing presence or absence of parasites, firmicutes, Bacteroidetes, absorption, inflammation, food sensitivities. Stool test results may describe presence, absence, and/or measurement of acetate, aerobic bacterial cultures, anerobic bacterial cultures, fecal short chain fatty acids, beta-glucuronidase, cholesterol, chymotrypsin, fecal color, *Cryptosporidium* EIA, *Entamoeba histolytica*, fecal lactoferrin, *Giardia lamblia* EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *Campylobacter* species, *Clostridium difficile, Cryptosporidium* species, *Cyclospora cayetanensis, Cryptosporidium* EIA, *Dientamoeba fragilis, Entamoeba histolytica, Escherichia coli, Entamoeba histolytica,* Giardia, *H. pylori,* Candida albicans, *Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge and subsequent urinary recovery using large molecules such as lactulose, polyethylene glycol-3350, and small molecules such as mannitol, L-rhamnose, polyethyleneglycol-400. Gut-wall body measurement may include data describing one or more images such as x-ray, MRI, CT scan, ultrasound, standard barium follow-through examination, barium enema, barium with contract, MRI fluoroscopy, positron emission tomography 9PET), diffusion-weighted MRI imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example Firmicutes species, Bacteroidetes species, Proteobacteria species, Verrumicrobia species, Actinobacteria species, Fusobacteria species, Cyanobacteria species and the like. Archaea may include methanogens such as Methanobrevibacter smithies' and Methanosphaera stadtmanae. Fungi may include *Candida* species and *Malassezia* species. Viruses may include bacteriophages. Microbiome species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as Ackerman's muciniphila, Anaerotruncus colihominis, bacteriology, *Bacteroides vulgates, Bacteroides-Prevotella, Barnesiella* species,

*Bifidobacterium longarm, Bifidobacterium species, Butyrivibrio crossotus, Clostridium* species, *Collinsella aerofaciens*, fecal color, fecal consistency, *Coprococcus eutactus, Desulfovibrio piger, Escherichia coli, Faecalibacterium prausnitzii*, Fecal occult blood, Firmicutes to Bacteroidetes ratio, *Fusobacterium* species, *Lactobacillus* species, *Methanobrevibacter smithii*, yeast minimum inhibitory concentration, bacteria minimum inhibitory concentration, yeast mycology, fungi mycology, *Odoribacter* species, *Oxalobacter* formigenes, parasitology, *Prevotella* species, *Pseudoflavonifractor* species, *Roseburia* species, *Ruminococcus* species, *Veillonella* species and the like.

With continued reference to FIG. 1, microbiome body measurement may include one or more stool tests results that identify all microorganisms living a user's gut including bacteria, viruses, archaea, yeast, fungi, parasites, and bacteriophages. Microbiome body measurement may include DNA and RNA sequences from live microorganisms that may impact a user's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of a user's body. This may include for example, lactose intolerance breath tests, methane based breath tests, hydrogen based breath tests, fructose based breath tests. *Helicobacter pylori* breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, nutrient as used herein, includes any substance required by the human body to function. Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient body measurement may include one or more blood test results that identify extracellular and intracellular levels of nutrients. Nutrient body measurement may include blood test results that identify serum, white blood cell, and red blood cell levels of nutrients. For example, nutrient body measurement may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient body measurement may include one or more blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosapentaenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient body measurement may include one or more salivary test results that identify levels of nutrients including any of the nutrients as described herein. Nutrient body measurement may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic body measurement may include one or more results from one or more blood tests, hair tests, skin tests, urine, amniotic fluid, buccal swabs and/or tissue test to identify a user's particular sequence of nucleotides, genes, chromosomes, and/or proteins. Genetic body measurement may include tests that example genetic changes that may lead to genetic disorders. Genetic body measurement may detect genetic changes such as deletion of genetic material or pieces of chromosomes that may cause Duchenne Muscular Dystrophy. Genetic body measurement may detect genetic changes such as insertion of genetic material into DNA or a gene such as the BRCA1 gene that is associated with an increased risk of breast and ovarian cancer due to insertion of 2 extra nucleotides. Genetic body measurement may include a genetic change such as a genetic substitution from a piece of genetic material that replaces another as seen with sickle cell anemia where one nucleotide is substituted for another. Genetic body measurement may detect a genetic change such as a duplication when extra genetic material is duplicated one or more times within a person's genome such as with Charcot-Marie Tooth disease type 1. Genetic body measurement may include a genetic change such as an amplification when there is more than a normal number of copies of a gene in a cell such as HER2 amplification in cancer cells. Genetic body measurement may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic body measurement may include a genetic change such as an inversion when one chromosome experiences two breaks and the middle piece is flipped or inverted before reattaching. Genetic body measurement may include a repeat such as when regions of DNA contain a sequence of nucleotides that repeat a number of times such as for example in Huntington's disease or Fragile X syndrome. Genetic body measurement may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic body measurement may include a genetic change such as monosomy such as when there is an absence of a chromosome instead of a pair, such as in Turner syndrome.

With continued reference to FIG. 1, genetic body measurement may include an analysis of COMT gene that is responsible for producing enzymes that metabolize neurotransmitters. Genetic body measurement may include an analysis of DRD2 gene that produces dopamine receptors in the brain. Genetic body measurement may include an analysis of ADRA2B gene that produces receptors for noradrenaline. Genetic body measurement may include an analysis of 5-HTTLPR gene that produces receptors for serotonin. Genetic body measurement may include an analysis of BDNF gene that produces brain derived neurotrophic factor. Genetic body measurement may include an analysis of 9p21 gene that is associated with cardiovascular disease risk. Genetic body measurement may include an analysis of APOE gene that is involved in the transportation of blood lipids such as cholesterol. Genetic body measurement may include an analysis of NOS3 gene that is involved in producing enzymes involved in regulating vaso-dilation and vaso-constriction of blood vessels.

With continued reference to FIG. 1, genetic body measurement may include ACE gene that is involved in producing enzymes that regulate blood pressure. Genetic body measurement may include SLCO1B1 gene that directs pharmaceutical compounds such as statins into cells. Genetic body measurement may include FUT2 gene that produces enzymes that aid in absorption of Vitamin B12 from digestive tract. Genetic body measurement may include MTHFR gene that is responsible for producing enzymes that aid in metabolism and utilization of Vitamin B9 or folate. Genetic body measurement may include SHMT1 gene that aids in production and utilization of Vitamin B9 or folate. Genetic body measurement may include MTRR gene that produces enzymes that aid in metabolism and utilization of Vitamin B12. Genetic body measurement may include MTR gene that produces enzymes that aid in metabolism and utilization of Vitamin B12. Genetic body measurement may include FTO gene that aids in feelings of satiety or fulness after eating. Genetic body measurement may include MC4R gene that aids in producing hunger cues and hunger triggers. Genetic body measurement may include APOA2 gene that directs body to produce ApoA2 thereby affecting absorption of saturated fats. Genetic body measurement may include UCP1 gene that aids in controlling metabolic rate and thermoregulation of body. Genetic body measurement may include TCF7L2 gene that regulates insulin secretion. Genetic body measurement may include AMY1 gene that aids in digestion of starchy foods. Genetic body measurement may include MCM6 gene that controls production of lactase enzyme that aids in digesting lactose found in dairy products. Genetic body measurement may include BCMO1 gene that aids in producing enzymes that aid in metabolism and activation of Vitamin A. Genetic body measurement may include SLC23A1 gene that produce and transport Vitamin C. Genetic body measurement may include CYP2R1 gene that produce enzymes involved in production and activation of Vitamin D. Genetic body measurement may include GC gene that produce and transport Vitamin D. Genetic body measurement may include CYP1A2 gene that aid in metabolism and elimination of caffeine. Genetic body measurement may include CYP17A1 gene that produce enzymes that convert progesterone into androgens such as androstenedione, androstendiol, dehydroepiandrosterone, and testosterone.

With continued reference to FIG. 1, genetic body measurement may include CYP19A1 gene that produce enzymes that convert androgens such as androstenedione and testosterone into estrogens including estradiol and estrone. Genetic body measurement may include SRD5A2 gene that aids in production of enzymes that convert testosterone into dihydrotestosterone. Genetic body measurement may include UFT2B17 gene that produces enzymes that metabolize testosterone and dihydrotestosterone. Genetic body measurement may include CYP1A1 gene that produces enzymes that metabolize estrogens into 2 hydroxy-estrogen. Genetic body measurement may include CYP1B1 gene that produces enzymes that metabolize estrogens into 4 hydroxy-estrogen. Genetic body measurement may include CYP3A4 gene that produces enzymes that metabolize estrogen into 16 hydroxy-estrogen. Genetic body measurement may include COMT gene that produces enzymes that metabolize 2 hydroxy-estrogen and 4 hydroxy-estrogen into methoxy estrogen. Genetic body measurement may include GSTT1 gene that produces enzymes that eliminate toxic by-products generated from metabolism of estrogens. Genetic body measurement may include GSTM1 gene that produces enzymes responsible for eliminating harmful by-products generated from metabolism of estrogens. Genetic body measurement may include GSTP1 gene that produces enzymes that eliminate harmful by-products generated from metabolism of estrogens. Genetic body measurement may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic body measurement may include blood tests, hair tests, skin tests, amniotic fluid, buccal swabs and/or tissue test to identify a user's metabolism. Metabolic body measurement may include blood tests that examine glucose levels, electrolytes, fluid balance, kidney function, and liver function. Metabolic body measurement may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic body measurement may include one or more blood, saliva, hair, urine, skin, and/or buccal swabs that examine levels of hormones within the body such as 11-hydroxy-androstereone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocrotisone, tetrahydrodeoxycortisol, allo-tetrahydrocortisol.

With continued reference to FIG. 1, metabolic body measurement may include one or more metabolic rate test results such as breath tests that may analyze a user's resting metabolic rate or number of calories that a user's body burns each day rest. Metabolic body measurement may include one or more vital signs including blood pressure, breathing rate, pulse rate, temperature, and the like. Metabolic body measurement may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin A1C test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1.

In an embodiment, a discovery center experience may include a companion, or friend, who may personalize user's optimal wellness journey by selecting a "genius friend" who is supplied with medical and nutritional information in order to specifically support user. In another embodiment, a discovery center experience may focus on a user's digestive path and gut health and include all the important steps through user's body that have an influence on gut health and wellbeing. The discovery center experience may include various medical equipment and machines. For example, the discovery center experience may include a microbiome test. A "microbiome" test as used in this disclosure is defined as a test to measure the microorganisms in a user's gastrointestinal (GI) tract. In another embodiment, the discovery center experience may include skin optimization health of a user which may include a skin elasticity measurement. A discovery center experience score 118 may be based on one or more discovery center experiences. In an embodiment, the discovery center experience online platform may generate a discovery center experience score 118. A discovery center experience score 118 may include a biological extraction 114 measurement of a user corresponding to a discovery center experience. In an embodiment, a biological extraction 114 may be received from a discovery center experience. A biological extraction 114, as used herein, may include any element and/or elements of data suitable for use as an element of the discovery center experience. At least a biological extraction 114 may include a physically extracted sample, which as used herein, includes a sample obtained by removing and analyzing tissue and/or fluid. Physically extracted sample may include without limitation a blood sample, a tissue sample, a buccal swab, a mucous sample, a stool sample, a hair sample, a fingernail sample, or the like. Physically extracted sample may include, as a non-limiting example, at least a blood sample. As a further non-limiting example, at least a biological extraction 114 may include at least a genetic sample. At least a genetic sample may include a complete genome of a person or any portion thereof. At least a genetic sample may include a DNA sample and/or an RNA sample. At least a biological extraction may include an epigenetic sample, a proteomic sample, a tissue sample, a biopsy, and/or any other physically extracted sample. At least a biological extraction 114 may include an endocrinal sample. As a further non-limiting example, the at least a biological extraction 114 may include a signal from at least a sensor configured to detect physiological data of a user and recording the at least a biological extraction as a function of the signal. At least a sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. At least a sensor may include any electromagnetic sensor, including without limitation electroencephalographic sensors, magnetoencephalographic sensors, electrocardiographic sensors, electromyographic sensors, or the like. At least a sensor may include a temperature sensor. At least a sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. At least a sensor may detect any hematological parameter including blood oxygen level, pulse rate, heart rate, pulse rhythm, and/or blood pressure. At least a sensor may be a part of at least a server 104 or may be a separate device in communication with at least a server 104.

A discovery center experience may be given a weight. "Weight", as used herein, may be multipliers or other scalar numbers reflecting a relative importance of a particular attribute or value. A weight may include, but is not limited to, a numerical value corresponding to an importance of an element. In some embodiments, a weighted value may be referred to in terms of a whole number, such as 1, 100, and the like. As a non-limiting example, a weighted value of 0.2 may indicate that the weighted value makes up 20% of the total value. As a non-limiting example, a discovery center experience may include the words "dairy free". A query may give a weight of 0.8 to the word "gluten", and a weight of 0.2 to the word "free". A query may map a plurality of semantic elements of query results having similar elements to the word "dairy" with differing elements than the word "free" due to the lower weight value paired to the word "dairy". Weighted values may be tuned through a machine-learning model, such as any machine learning model as described throughout this disclosure without limitation. In some embodiments, a query may generate weighted values based on prior queries. In some embodiments, a query may be configured to filter out one or more "stop words" that may not convey meaning, such as "of," "a," "an," "the," or the like. In an embodiment, apparatus 138 may be configured to retrieve a plurality of nutrient labels 126 describing a plurality of nutrients. For example, a plurality of nutrient labels 126 may include data related to various nutrients such as the level of Vitamin C in an orange.

With continued reference to FIG. 1B, apparatus 138 may be configured to generate at least an importance factor of a nutrient 130. "Nutrient" as used in this disclosure is defined as a substance that provides nourishment essential for growth and the maintenance of life. The opposite of a nutrient may be a toxin which is defined as molecules that are capable of causing disease on contact with or absorption by body tissues interacting with biological macromolecules such as enzymes or cellular receptors. A "nutrient importance factor" as used in this disclosure is defined as the proprietary calculation to establish importance of nutrients/toxins based on impact (positive or negative) on human physiology, storage in the body, number of physiological functions and biochemical processes. In an embodiment, computing device 102 may utilize the discovery center experience score 118 and user biological extraction 114 data to influence the nutrient importance factor score 130. For example, if it is determined that a user's bone health is poor, then the nutrient calcium will be more important to user than a nutrient like folate, which is used for heart health. By way of another example, if it is determined that user's bone health is poor, then foods with high levels of calcium may be recommended and displayed to user and foods high in calcium such as milk, eggs, salmon may be displayed and ranked higher than foods low in calcium such as bread and apples. Nutrient importance factor 130 may also be used to recommend meals. For example, if it is determined that user has poor gut health and low iron levels, nutrient importance factor of iron may be ranked high along with nutrients which aid in absorbing iron such as a Vitamin C. The importance factor of a nutrient 130 may be used with phenotype optimal nutrient targets to calculate a nutrition score. A phenotype nutrient importance factor may be important to human physiological function. For example, if the phenotype nutrient is essential to human physiological function, it may be given a factor of 5. If the phenotype nutrient is conditionally essential, a factor of 3 may be given. Similarly, if the phenotype nutrient is nonessential, it may be given a factor of 1. Furthermore, if the phenotype nutrient has no biological function, it may be given a factor of 0 and if it is harmful then a factor of −1 may be assigned. In addition, a degree of importance may be taken into consideration. For example, if deficiency would lead to potential death then a factor of 5 may be assigned, if optimal intake is associated with a reduced risk of chronic disease then a factor of 5 may also be assigned. Similarly, if a deficiency may lead to potential individual or multiple systems failure then a factor of 4 may be assigned, if a deficiency would lead to potential system inadequacies resulting in neurological symptoms a factor of 3 may be assigned, if a deficiency may lead to potential system inadequacies resulting in physical expression a factor of 2 may be assigned. If a deficiency has not been documented a factor of 1 may be assigned, similarly if excess or regular intake may be associated with chronic disease then a factor of −1 may be assigned. The amount of time of storage in user's body may also affect the phenotype nutrient importance factor. For example, if it is not stored more than a day then a factor of 5 may be assigned, if it is minimally stored for 1 to 5 days then a factor of 3 may be assigned, if it is significantly stored, more than 5 days then a factor of 1 may be assigned. Physiological functions of a nutrient may also be taken into account. "Physiological function" as used in this disclosure is defined as the special action or physiologic property of an organ or other part of the body. For example, if a nutrient has more than 3 different functions it may receive a score of 5, if there are 2 different functions a score of 4 may be assigned and if there is 1 function a score of 3 may be assigned. Physiological functions may include, without limitation, energy production, enzyme cofactor, coenzyme, precursor, cell signaling, cell differentiation, antioxidant, gene expression, structural, regulatory, catalytic functions and the like. For example, B12 may be a cofactor for methionine synthase and L-methylmalonym-coenzyme A mutase and may consist of 1 function and a cofactor/score of 3. By way of another example, Vitamin C which is a potent antioxidant, and essential cofactor in numerous enzymatic reactions and is involved in the structure of collagen (among others) and the regulation of gene expression has 4 functions and may be assigned a score of 4.

In an embodiment, biochemical processes of a nutrient may also be assigned an importance factor of a nutrient 130. For example, if a nutrient has more than 10 biochemical processes it may receive a score of 5, if a nutrient has 5-9 biochemical processes it may be assigned a score of 4, if it has 2-4 biochemical processes it may be assigned a score of 3 and if it has 1 biochemical process it may be assigned a score of 2. Additionally, if it adversely affects biochemical processes then a score of −1 may be assigned. For example, vitamin B12 is involved in 2 major biochemical processes as a cofactor therefore has a score of 3. By way of another example, Vitamin C is a cofactor for at least 11 various biochemical reactions and may be assigned a score of 5. For example, it may be advantageous to calculate the phenotype nutrient importance factor for Niacin. "Niacin" as used in this disclosure is defined as Niacin, is an organic compound (also known as a nicotinic acid), and a form of vitamin $B_3$, an essential human nutrient and may be manufactured by plants and animals from the amino acid tryptophan. For example, niacin is an essential micronutrient, and deficiency can lead to death. It is not stored in the body and functions in redox reactions, coenzyme, deacetylaition, ADP-ribosylation, calcium mobilization and more than 400 enzymes require niacin coenzymes for redox reactions.

Still referring to FIG. 1B, determining the importance factor of a nutrient 130 may include utilizing a machine learning model 122. A "machine-learning model," as used in this disclosure, is a mathematical and/or algorithmic representation of a relationship between inputs and outputs, as generated using any machine-learning process including without limitation any process as described above and stored in memory, an input is submitted to a machine-learning model once created, which generates an output based on the relationship that was derived. Training data may include discovery center score input. Machine-learning module may perform determinations, classification, and/or analysis steps, methods, processes, or the like as described in this disclosure using machine learning processes. A "machine learning process," as used in this disclosure, is a process that automatedly uses training data to generate an algorithm that will be performed by a computing device/module to produce outputs given data provided as inputs; this is in contrast to a non-machine learning software program where the commands to be executed are determined in advance by a user and written in a programming language. In one or more embodiments, a machine-learning module may be generated using training data. Training data may include inputs and corresponding predetermined outputs so that machine-learning module may use the correlations between the provided exemplary inputs and outputs to develop an algorithm and/or relationship that then allows machine-learning module to determine its own outputs for inputs. Training data may contain correlations that a machine-learning process may use to model relationships between two or more categories of data elements. The exemplary inputs and outputs may come from a database, such as any database described in this disclosure. For example, discovery center experience score 118 inputs may include user biological extraction 114 data and outputs may include the importance factor of a nutrient 130. In other embodiments, machine-learning module 122 may obtain discovery center experience score 118 training data by querying a communicatively connected database that includes past inputs and outputs of the machine learning model 122. In an embodiment the apparatus 100 may be further configured to determine the importance factor of a nutrient 130, wherein determining the importance factor of a nutrient 130 further includes receiving discovery center experience score 118 training data correlating biological extraction data elements to a discover center experience data elements; training a machine learning model as a function of the biological extraction data and outputting the importance factor of a nutrient 130 as a function of the machine learning model.

Training data may include inputs from various types of databases, resources, and/or user inputs and outputs correlated to each of those inputs so that a machine-learning module may determine an output. Correlations may indicate causative and/or predictive links between data, which may be modeled as relationships, such as mathematical relationships, by machine-learning processes, as described in further detail below. In one or more embodiments, training data may be formatted and/or organized by categories of data elements by, for example, associating data elements with one or more descriptors corresponding to categories of data elements. As a non-limiting example, training data may include data entered in standardized forms by persons or processes, such that entry of a given data element in a given field in a form may be mapped to one or more descriptors of categories. In an embodiment, apparatus 138 may be configured to display the importance factor of a nutrient of a plurality of nutrients to a user on a user display 134.

Referring now to FIG. 1A, at least a server 104 is designed and configured to generate at least a vibrant compatibility plan 192 wherein the at least a vibrant compatibility plan 192 further comprises a plurality of compatible food elements each containing at least a food element compatibility index value as a function of the at least a hierarchical clustering model 160. Vibrant compatibility plan 192, as used herein, includes any information and data containing a list of food elements each containing at least a food element compatibility index value. For example and without limitation, vibrant compatibility plan 192 may include a list of two hundred food elements each containing at least a food element compatibility index value. In an embodiment, two hundred food elements may be arranged in a hierarchical manner and ranked according to compatibility. For example, vibrant compatibility plan 192 may include a ranking in order of decreasing compatibility of two hundred food elements.

With continued reference to FIG. 1A, at least a server 104 is configured to generate at least a vibrant compatibility plan 192 containing a sequencing instruction set wherein the sequencing instruction set contains at least an optimal combination of at least a first compatible food element and at least a second compatible food element as a function of the at least a desired dietary state. Sequencing instruction set may include information and/or data describing optimal combinations of foods and ingredients that a user may combine to create meals or that when combined together may optimize the nutrition of each other as a function of a user's desired dietary state. For instance and without limitation, sequencing instruction set may include information describing optimal combinations of a first compatible food element such as red kidney beans and a second compatible food element such as brown rice for a user with a desired dietary state of vegan diet. In yet another non-limiting example, sequencing instruction set may include information describing optimal combinations of a first compatible food element such as wild Alaskan salmon with a second compatible food element such as avocado for a user with a desired dietary state of ketogenic diet. In yet another non-limiting example, sequencing instruction set may include information describing optimal combinations of a first compatible food element such as bananas and a second compatible food element such as blueberries for a user with a desired dietary state of low FODMAP diet.

Figure 2:
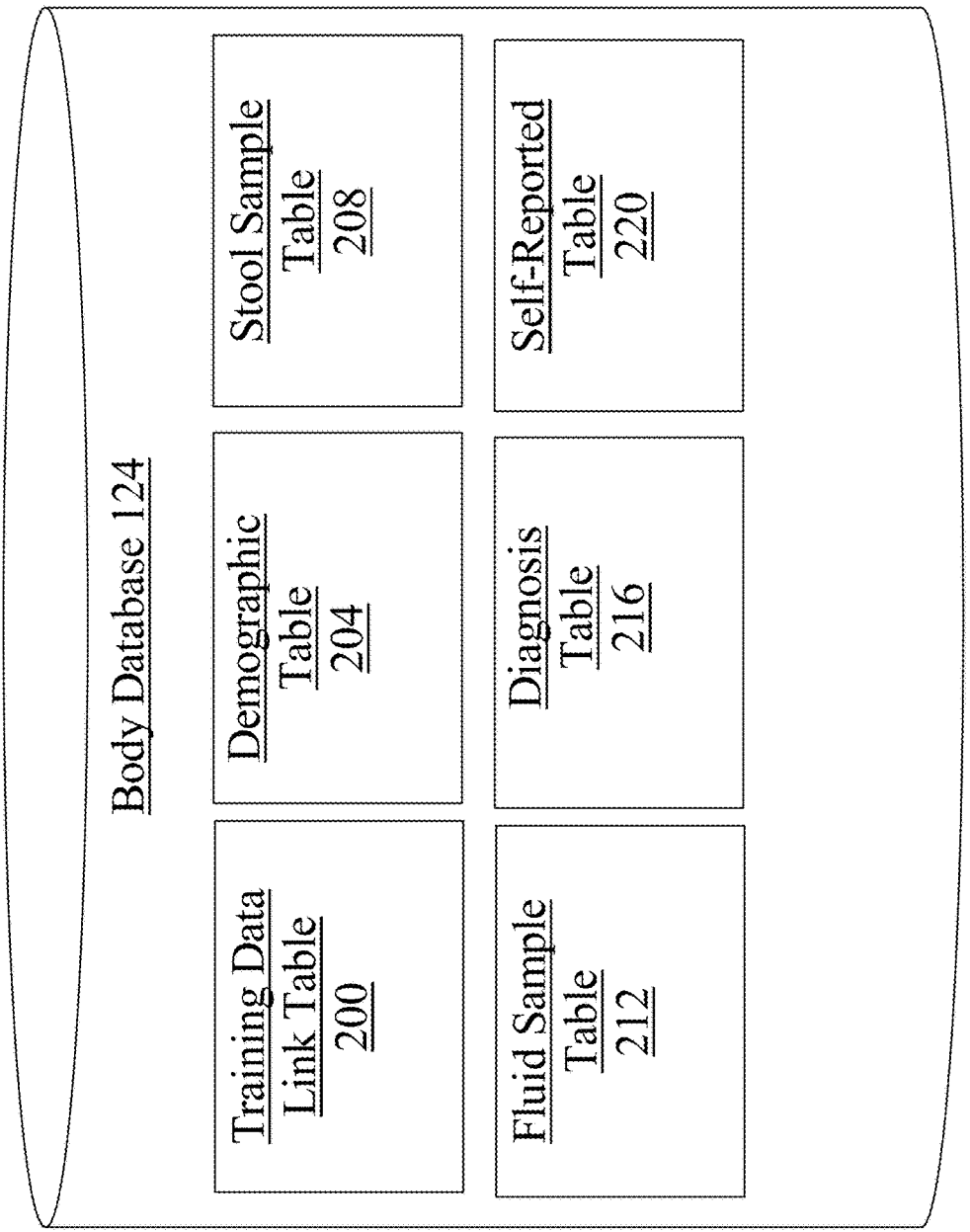
FIG. 2 is a block diagram illustrating an exemplary embodiment of a body database.

Referring now to FIG. 2, an exemplary embodiment of body database 124 is illustrated, which may be implemented, without limitation, as a hardware or software module. Body database 124 may be implemented, without limitation, as a relational database, a key-value retrieval datastore such as a NOSQL database, or any other format or structure for use as a datastore that a person skilled in the art would recognize as suitable upon review of the entirety of this disclosure. Body database 124 may contain datasets that may be utilized by unsupervised learning module 156 to find trends, cohorts, and shared datasets between data contained within body database 128 and composition datum 108. In an embodiment, datasets contained within body database 124 may be categorized and/or organized according to shared characteristics. For instance and without limitation, one or more tables contained within body database 124 may include training data link table 200; training data link table 200 may contain information linking datasets contained within body database 124 to datasets contained within training set database 180. For example, dataset contained within body database 124 may also be contained within training set database 180 which may be linked through training data link table 200. In yet another non-limiting example, training data link table 200 may contain information linking data sets contained within body database 124 to datasets contained within training set database 180 such as when dataset and training set may include data sourced from the same user or same cohort of users, or when dataset is utilized as training set. One or more tables contained within body database 124 may include demographic table 204; demographic table 204 may include datasets classified to demographic information. Demographic information may include datasets describing age, sex, ethnicity, socioeconomic status, education level, marital status, income level, religion, offspring information, and the like. One or more tables contained within body database 124 may include stool sample table 208; stool sample table 208 may include datasets classified to stool samples. Stool samples may include datasets describing stool levels of nutrition biomarkers including for example, measured values from a stool sample of anaerobes, parasites, firmicutes to Bacteroidetes ratio, absorption, inflammation, sensitivities, parasitology and the like. One or more tables contained within body database 124 may include fluid sample table 212; fluid sample table 212 may include datasets classified to fluid samples. Fluid samples may include datasets describing fluid samples analyzed for nutritional biomarkers including for example urine sample, semen sample, sweat sample, amniotic fluid sample, cerebrospinal fluid, synovial fluid sample, pleural fluid sample, pericardial fluid sample, blood sample, salivary sample, and the like. One or more tables contained within body database 124 may include diagnosis table 216; diagnosis table 216 may include datasets containing diagnostic information. Diagnostic information may include identification of an illness or health problem by a medical professional including for example, an informed advisor such as a functional medicine doctor, a nutritionist, an herbalist, an acupuncturist, a dietician, a nurse, and the like. One or more tables contained within body database 124 may include self-reported table 220; self-reported table 220 may include datasets containing self-reported nutritional states. Self-reported nutritional states may include for example, a user self-report to eliminate gluten due to bloating or a user self-report to eliminate meat for ethical reasons. One or more tables contained within body database 124 may include tissue sample table, nutrient biomarker table, chief complaint table, (not pictured). Persons skilled in the art will be aware of the various database tables that may be contained within body database 124 consistently within the purview of this disclosure.

Figure 3:
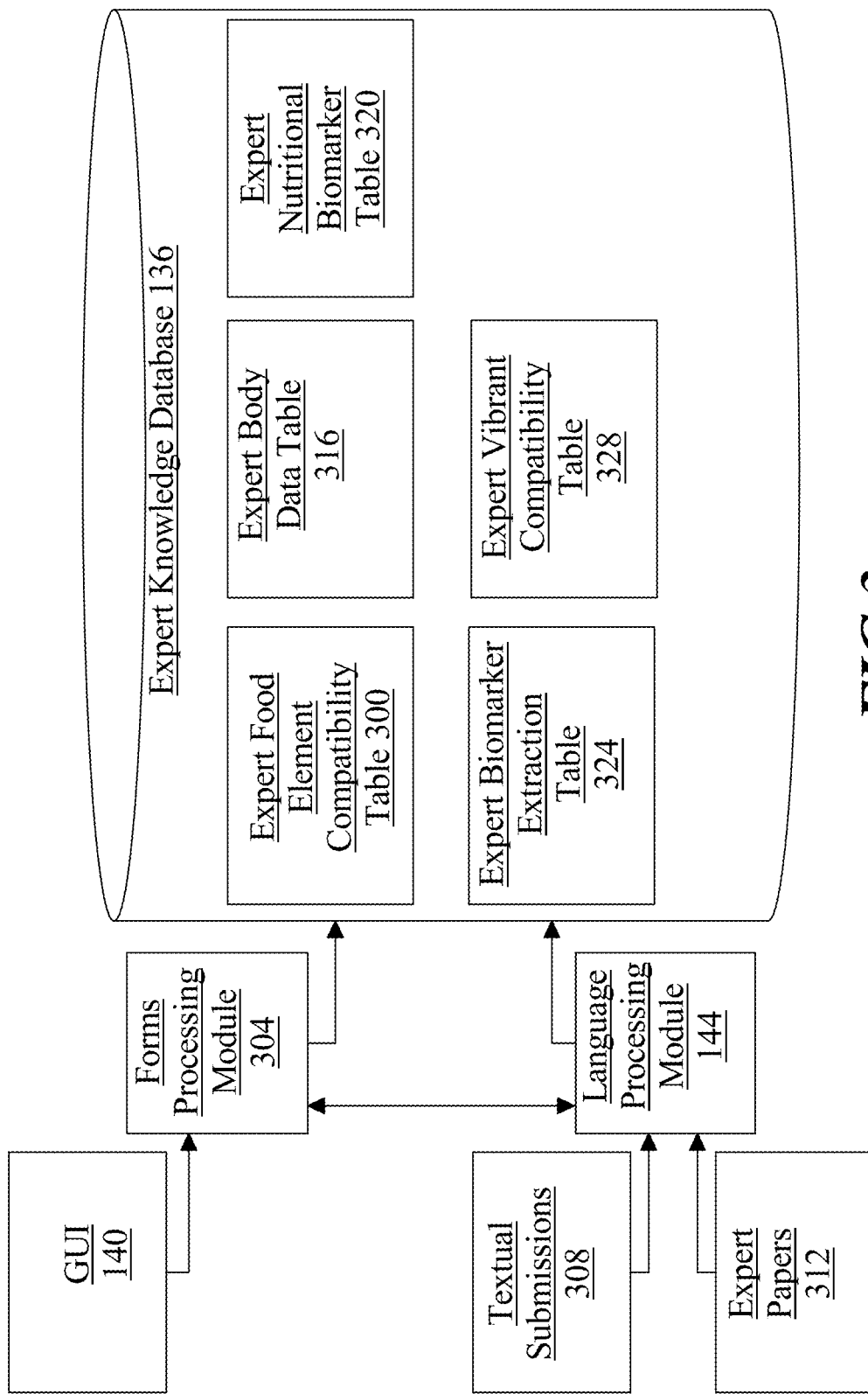
FIG. 3 is a block diagram illustrating an exemplary embodiment of an expert knowledge database.

Referring now to FIG. 3, an exemplary embodiment of expert knowledge database 136 is illustrated. Expert knowledge database 136 may include any data structure for ordered storage and retrieval of data, which may be implemented as a hardware or software module, and which may be implemented as any database structure suitable for use as body database 124. One or more database tables in expert knowledge database 136 may include, as a non-limiting example, an expert food element compatibility table 300. Expert food element compatibility table 300 may be a table relating user body data 116 to compatible food elements; for instance, where an expert has entered data relating a user body datum such as high triglycerides to a compatible food element such as oat bran, one or more rows recording such an entry may be inserted in expert food element compatibility table. In an embodiment, a forms processing module 304 may sort data entered in a submission via graphical user interface 140 by, for instance, sorting data from entries in the graphical user interface 140 to related categories of data; for instance, data entered in an entry relating in the graphical user interface 140 to a body datum may be sorted into variables and/or data structures for storage of body datums, while data entered in an entry relating to compatible food elements and/or an element thereof may be sorted into variables and/or data structures for the storage of, respectively, categories of compatible food elements. Where data is chosen by an expert from pre-selected entries such as drop-down lists, data may be stored directly; where data is entered in textual form, language processing module 144 may be used to map data to an appropriate existing label, for instance using a vector similarity test or other synonym-sensitive language processing test to map classified biomarker data to an existing label. Alternatively or additionally, when a language processing algorithm, such as vector similarity comparison, indicates that an entry is not a synonym of an existing label, language processing module 144 may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 308, such as accomplished by filling out a paper or PDF form and/or submitting narrative information, may likewise be processed using language processing module 144. Data may be extracted from expert papers 312, which may include without limitation publications in medical and/or scientific journals, by language processing module 144 via any suitable process as described herein. Persons skilled in the art, upon reviewing the entirety of this disclosure, will be aware of various additional methods whereby novel terms may be separated from already-classified terms and/or synonyms therefore, as consistent with this disclosure. Expert food element compatibility table 300 may include a single table and/or a plurality of tables; plurality of tables may include tables for particular categories of food elements such as a vegetable table, a fruit table, an animal protein table, a seafood table, a spice table, a fat table, a grain table, and the like(not shown), to name a few non-limiting examples presented for illustrative purposes only.

With continued reference to FIG. 3, one or more database tables in expert knowledge database 136 may include, an expert body data table 316 may list one or more body datums as described by experts, and one or more compatible food products associated with body datum. For example, a body datum such as a blood test showing elevated glucose levels may be associated with one or more compatible food products such as animal protein, vegetables, and oils. As a further example an expert nutritional biomarker table 320 may list one or more nutritional biomarkers as described and input by experts and associated physiological classifications one or more nutritional biomarkers may be classified into as well as desired dietary state. For instance and without limitation, an expert biomarker table 320 may include one or more tables detailing biomarkers commonly associated with a particular diet such as Paleo diet or ketogenic diet and the like. In yet another non-limiting example, expert biomarker table 320 may include one or more tables detailing biomarkers commonly associated with a particular physiological system such as the gastrointestinal system or the neurological system. As an additional example, an expert biomarker extraction table 324 may include information pertaining to biological extraction and/or medical test or collection necessary to obtain a particular nutritional biomarker, such as for example a tissue sample that may include a urine sample, blood sample, hair sample, cerebrospinal fluid sample, buccal sample, sputum sample, and the like. As an additional example, an expert vibrant compatibility table 328 may include one or more tables detailing vibrant compatibility plan 192 associated with one or more elements of body data, biomarker data and the like. For example, expert vibrant compatibility table 328 may include information detailing hierarchies of compatible food elements for a particular body datum such as a body datum reflecting lactose intolerance may contain compatible food elements ranked as highly compatible to include buckwheat, amaranth, and celery ranked as highly compatible while cow yogurt, goat cheese, and cow milk may be ranked as being of very low compatibility. Tables presented above are presented for exemplary purposes only; persons skilled in the art will be aware of various ways in which data may be organized in expert knowledge database 136 consistently with this disclosure.

Figure 4:
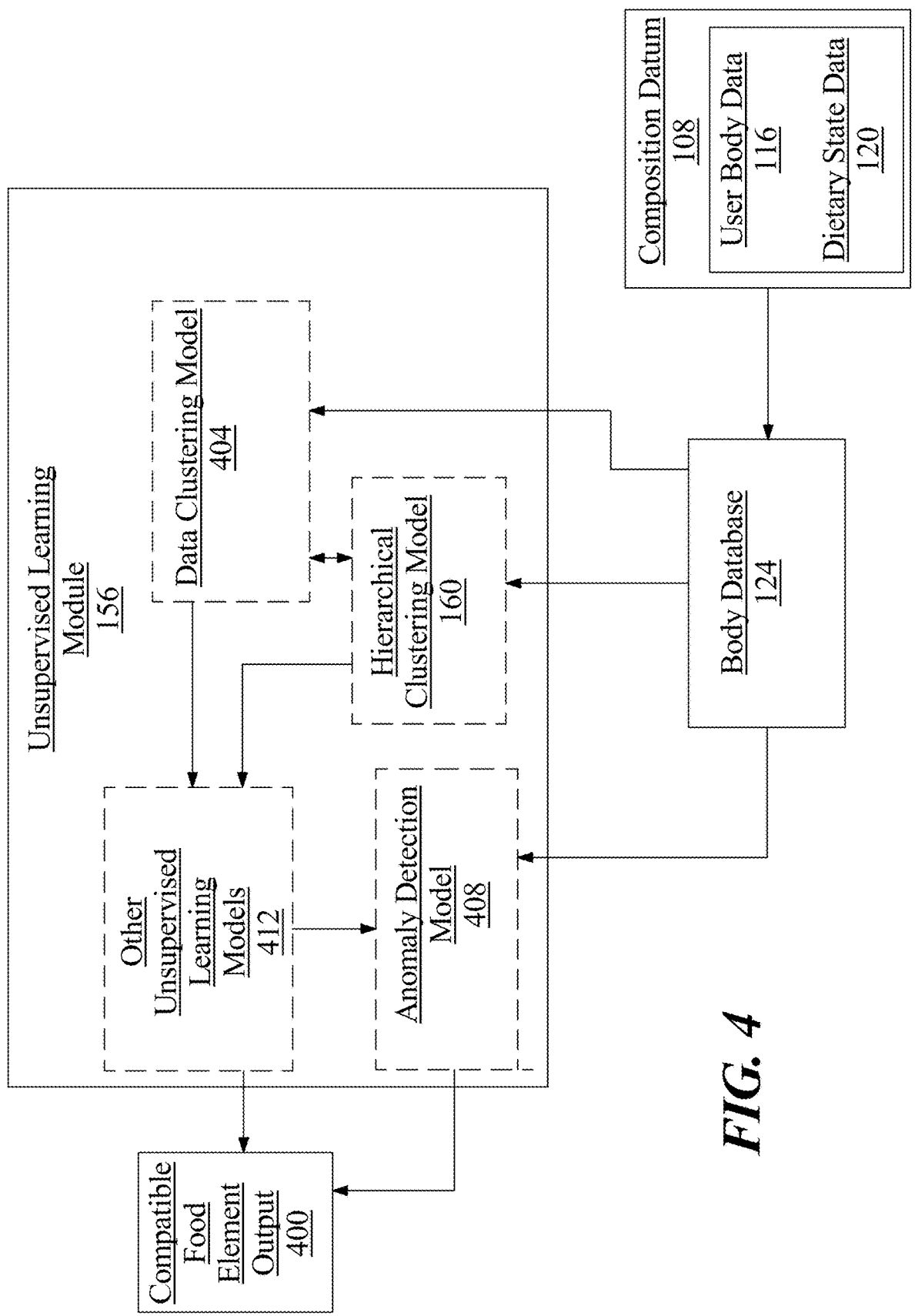
FIG. 4 is a block diagram illustrating an exemplary embodiment of an unsupervised learning module.

Referring now to FIG. 4, an exemplary embodiment of unsupervised learning module 156 is illustrated. Unsupervised learning may include any of the unsupervised learning processes as described herein. Unsupervised learning module 156 generates at least a hierarchical clustering model 160 to output at least a compatible food element 400 as a function of the at least a composition datum 108 and the at least a correlated dataset. Correlated dataset may be selected from body database 124 as described below in more detail in reference to FIG. 5. Body database 124 may contain data describing different users with different nutritional biomarkers and demographics of users, which may be organized into categories contained within body database 124 as described above in more detail in reference to FIG. 2. Hierarchical clustering model 160 may group and/or segment datasets into hierarchy clusters including both agglomerative and divisive clusters. Agglomerative clusters may include a bottom up approach where each observation starts in its own cluster and pairs of clusters are merged as one moves up the hierarchy. Divisive clusters may include a top down approach where all observations may start in one cluster and splits are performed recursively as one moves down the hierarchy. In an embodiment, hierarchical clustering model 160 may analyze datasets obtained from body database 124 to find observations which may each initially form own cluster. Hierarchical clustering model 160 may then identify clusters that are closest together and merge the two most similar clusters and continue until all clusters are merged together. Hierarchical clustering model 160 may output a dendrogram which may describe the hierarchical relationship between the clusters. Distance between clusters that are created may be measured using a suitable metric. Distance may be measured between for example the two most similar parts of a cluster known as single linkage, the two least similar bits of a cluster known as complete-linkage, the center of the clusters known as average-linkage or by some other criterion which may be obtained based on input received from expert knowledge database 136 for example.

With continued reference to FIG. 4, unsupervised learning module 156 may perform other unsupervised learning models to output at least a compatible food element output. Unsupervised learning module 156 may generate a data clustering model 404. Data clustering model 404 may group and/or segment datasets with shared attributes to extrapolate algorithmic relationships. Data clustering model 404 may group data that has been labelled, classified, and/or categorized. Data clustering model may identify commonalities in data and react based on the presence or absence of such commonalities. For instance and without limitation, data clustering model 404 may identify other data datasets that contain the same or similar nutritional biomarker contained within composition datum 108 or identify other datasets that contain users with similar demographics and/or background information. In an embodiment, data clustering model 404 may cluster data and generate labels that may be utilized as training set data. Data clustering model 404 may utilize other forms of data clustering algorithms including for example, hierarchical clustering, k-means, mixture models, OPTICS algorithm, and DBSCAN.

With continued reference to FIG. 4, unsupervised learning module 156 may generate an anomaly detection model 408. Anomaly detection model 408 may include identification of rare items, events or observations that differ significant from the majority of the data. Anomaly detection model 408 may function to observe and find outliers. For instance and without limitation, anomaly detect may find and examine data outliers such as a nutritional biomarker that is not compatible with any food elements or that is compatible with very few food elements.

With continued reference to FIG. 4, unsupervised learning module 156 may generate other unsupervised learning models 412. This may include for example, neural networks, autoencoders, deep belief nets, Hebbian learning, adversarial networks, self-organizing maps, expectation-maximization algorithm, method of moments, blind signal separation techniques, principal component analysis, independent component analysis, non-negative matrix factorization, singular value decomposition (not pictured).

Figure 5:
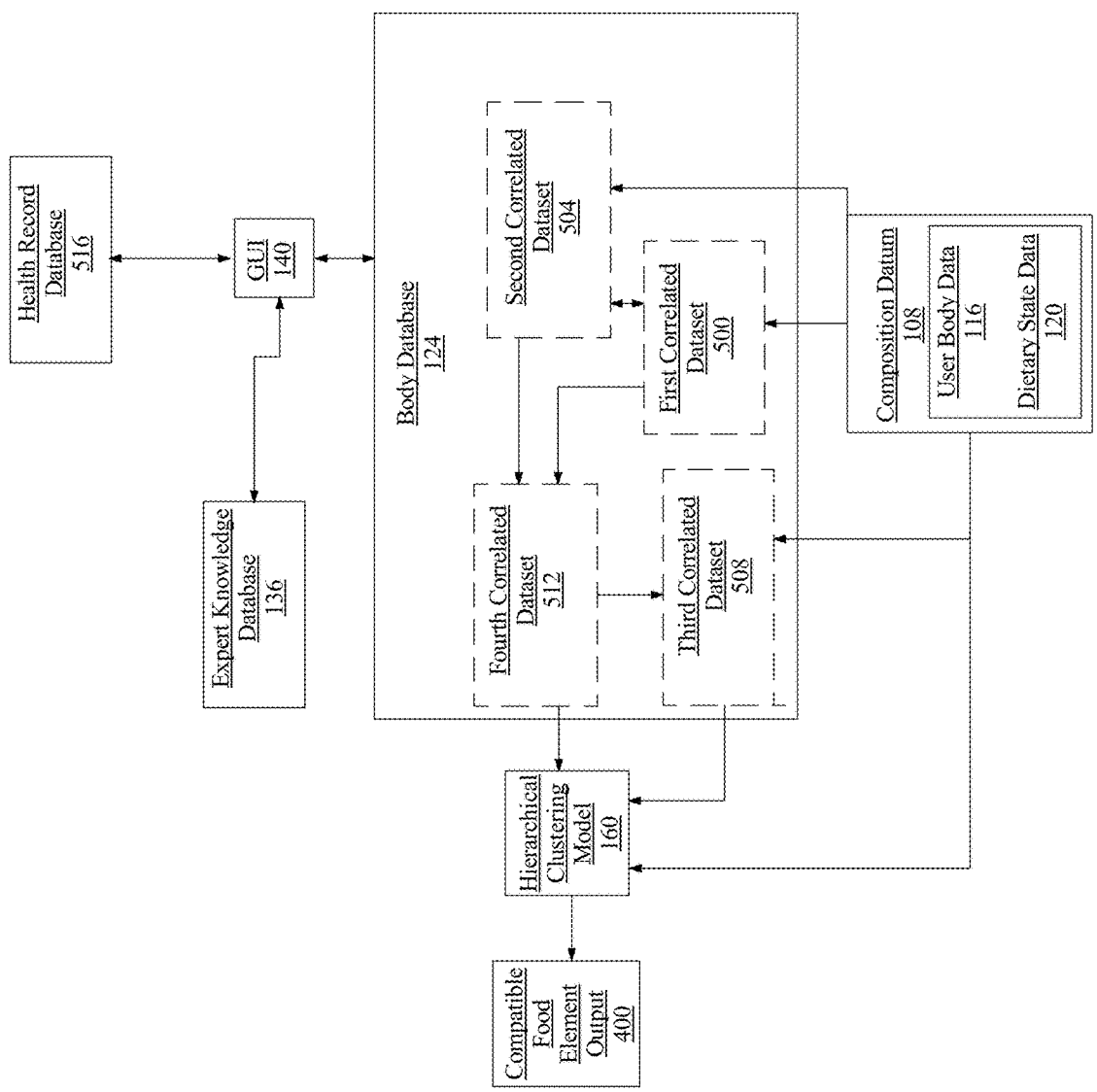
FIG. 5 is a block diagram illustrating an exemplary embodiment of a hierarchical clustering model.

Referring now to FIG. 5, an exemplary embodiment of hierarchical clustering model 160 is illustrated. Composition datum 108 containing an element of user body data 116 and an element of dietary state data 120 is utilized to select at least a correlated dataset from body database. In an embodiment, datasets contained within body database 124 may be organized into categories that each may be selected as a function of composition datum 108 as described above in more detail in reference to FIG. 2. For example, first correlated dataset 500 may be categorized as demographics and may contain datasets relating to demographics that may be utilized when generating hierarchical clustering model 160. In such an instance, second correlated dataset 504 may be categorized as fluid sample dataset that may contain datasets containing information relating to a particular nutritional biomarker extracted from a fluid sample that relates to fluid sample contained within user body data 116. In such an instance, third correlated dataset 508 may be categorized as diagnostic dataset, that may include contain data entries containing the same diagnosis as a user. In such an instance, fourth correlated dataset 512 may be categorized as socioeconomic dataset, that may contain data entries obtained from sources that are of a particular socioeconomic background related to user.

With continued reference to FIG. 5, datasets contained within body database may be obtained from a plurality of sources. Datasets contained within body database may be received from expert input such and contained within expert knowledge database 136 as described above in more detail in reference to FIG. 3. In an embodiment, experts such as leading functional medicine practitioners and scientists may provide input through GUI 140 whereby such information may be contained within expert knowledge database 136. Datasets contained within body database 124 may also be obtained from health record database 516, which may contain datasets obtained from different sources such as deidentified medical records as described below in more detail in reference to FIG. 6. Datasets selected from body database 124 by at least a server 104 may be utilized in combination with composition datum 108 to generate hierarchical clustering model 160. Hierarchical clustering model 160 outputs at least a compatible food element. Compatible food element includes any of the compatible food elements as described herein.

Figure 6:
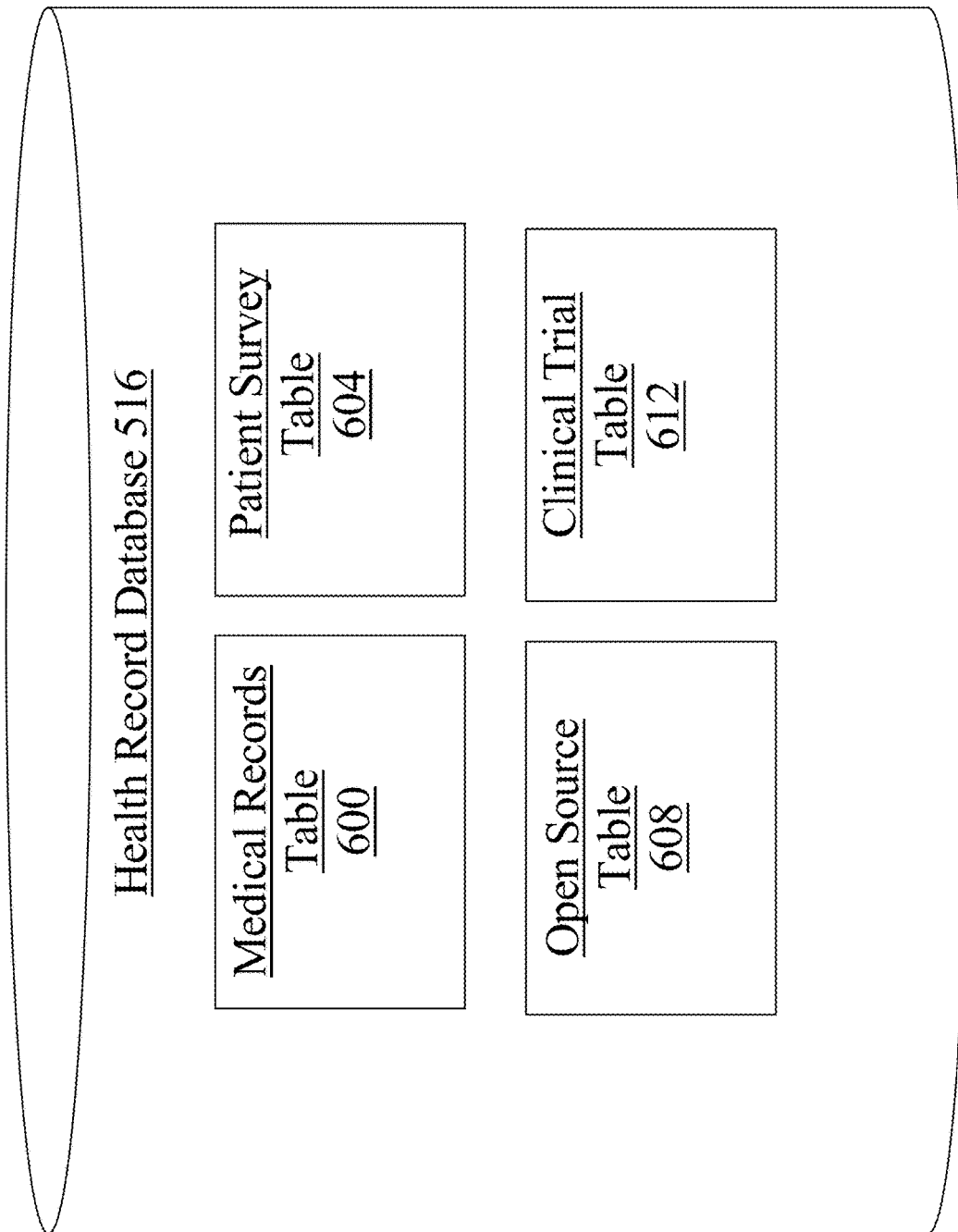
FIG. 6 is a block diagram illustrating an exemplary embodiment of a health record database.

Referring now to FIG. 6, an exemplary embodiment of health record database 516 is illustrated. Health record database 516 may include any data structure for ordered storage and retrieval of data, which may be implemented as a hardware or software module, and which may be implemented as any database structure suitable for use as body database 124. Health record database 516 may include datasets input from a plurality of sources that may be used as datasets by body database 124 and/or training set database 180. One or more tables contained within health record database 516 may include, as a non-limiting example, medical records table 600; medical records table 600 may include data obtained from medical records. Medical records table 600 may include medical record data that may be sourced from physicians, electronic health records, hospitals, nursing homes, skilled nursing facilities, health insurance companies and the like. One or more tables contained within health record database 516 may include, as a non-limiting example, patient survey table 604; patient survey table 604 may include data obtained from patient surveys. Patient survey table 604 may include patient surveys obtained from patients in specific geographic areas, specific socioeconomic backgrounds, patients with particular health problems, and the like. One or more tables contained within health record database 516 may include, as a non-limiting example, open source table 608; open source table 608 may include data obtained from open sources. Open source table 608 may include data obtained from open sources such as government sources and websites that may contain data available for use by anyone. One or more tables contained within health record database 516 may include, as a non-limiting example, clinical trial table 612; clinical trial table 612 may include data obtained from clinical trials. Clinical trial table 612 may include information obtained for example from clinical trials at research centers and academic institutions.

Figure 7:
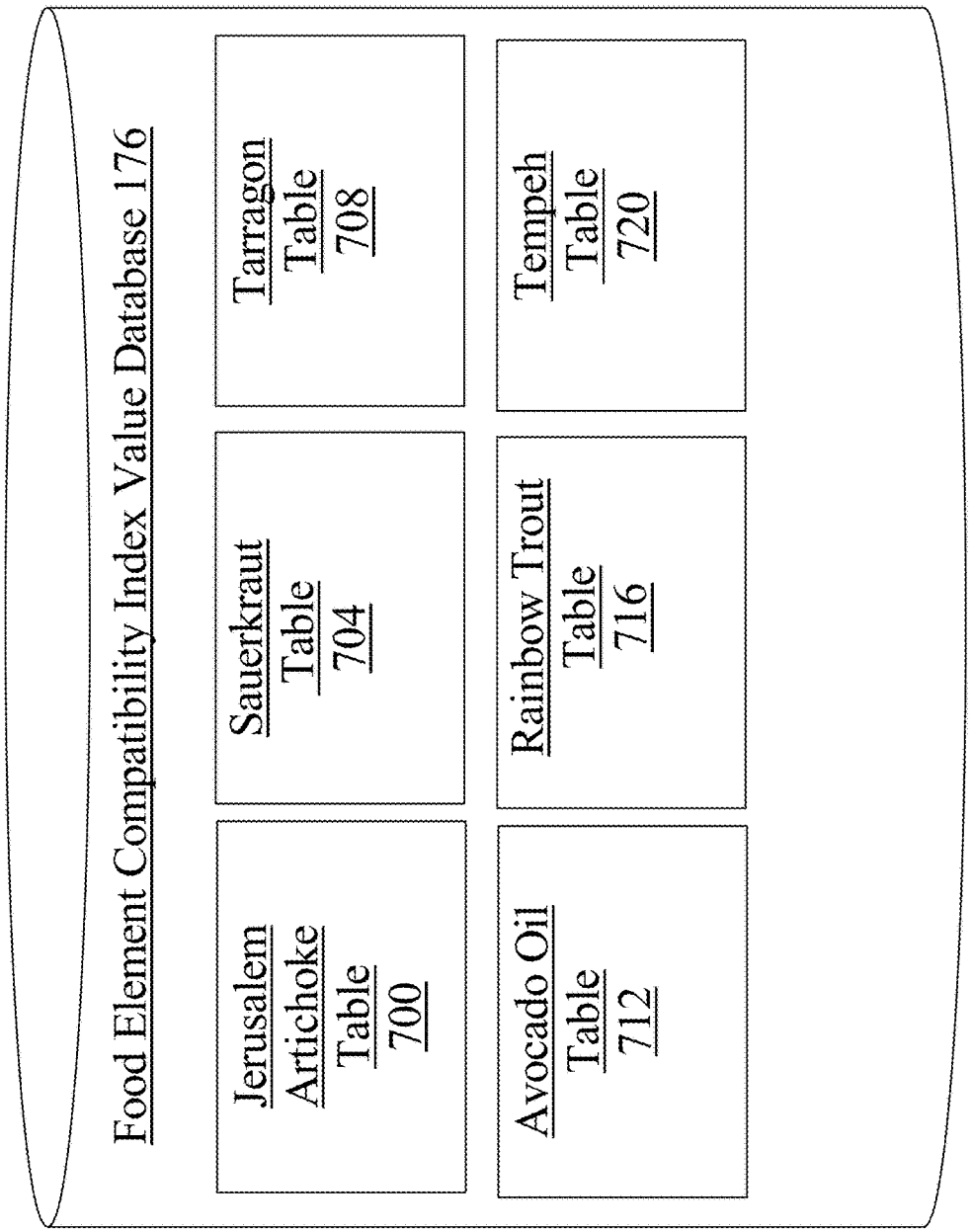
FIG. 7 is a block diagram illustrating an exemplary embodiment of a food element compatibility index value database.

Referring now to FIG. 7, an exemplary embodiment of food element compatibility index value database 168 is illustrated. Food element compatibility index value database 168 may include any data structure for ordered storage and retrieval of data, which may be implemented as a hardware or software module, and which may be implemented as any database structure suitable for use as body database 124. Food element compatibility index value database 168 may contain information describing compatible substance index values for individual food elements. Food element compatibility index value database 168 may be consulted by at least a server 104 when generating at least a vibrant compatibility plan 192. Food element compatibility index value database 168 may be consulted by at least a server 104 when ranking food elements. Food element compatibility index value database 168 may contain food element compatibility index value for individual food elements and each compatibility index value for each food linked to a particular body datum, nutritional biomarker, and/or dietary state. Food element compatibility index value database 168 may also contain food element compatibility index values for combinations of multiple food elements and compatibility of a second compatibility food element as a function of selecting a first compatibility food element based on food element compatibility index value as described above in more detail in reference to FIG. 1. One or more database tables contained within food element compatibility index value database 168 may include Jerusalem artichoke table 700; Jerusalem artichoke table 700 may include compatibility index values for Jerusalem artichoke for any given nutritional biomarker, body datum, and compatibility index values for Jerusalem artichoke as compared to other compatible food elements for any given biomarker and/or body datum. For example, Jerusalem artichoke may have a high compatibility index value for a biomarker that shows low gastrointestinal levels of *Streptococcus* and *Lactobacillus* but may have a low compatibility index value for a biomarker that shows overgrowth of *Candida*. One or more database tables contained within food element compatibility index value database 168 may include sauerkraut table 704; sauerkraut table 704 may include compatibility index values for sauerkraut for any given nutritional biomarker, body datum, and compatibility index values for sauerkraut as compared to other compatible food elements for any given biomarker and/or body datum. For example and without limitation, sauerkraut may have a high compatibility index value for a dietary state such as paleo but may have a low compatibility index value for a dietary state such as yeast-free diet. One or more database tables contained within food element compatibility index value database 168 may include tarragon table 708; tarragon table 708 may include compatibility index values for tarragon for any given nutritional biomarker, body datum, and compatibility index values for tarragon as compared to other compatible food elements for any given biomarker and/or body datum. One or more database tables contained within food element compatibility index value database 168 may include avocado oil table 712; avocado oil 712 may include may include compatibility index values for avocado oil for any given nutritional biomarker, body datum, and compatibility index values for avocado as compared to other compatible food elements for any given biomarker and/or body datum. For example, avocado oil may contain a high compatibility index value when substituted to selected as a function of an avocado. One or more database tables contained within food element compatibility index value database 168 may include rainbow trout table 716; rainbow trout table 716 may include may include compatibility index values for rainbow trout for any given nutritional biomarker, body datum, and compatibility index values for avocado as compared to other compatible food elements for any given biomarker and/or body datum. For example, rainbow trout may have a high compatibility index value as compared to compatibility index value for brown trout, indicating a high likelihood that rainbow trout may be substituted and/or selected as a function first selecting brown trout. One or more database tables contained within food element compatibility index value database 168 may include tempeh table 720; tempeh table 720 may include compatibility index values for tempeh for any given nutritional biomarker, body datum, and compatibility index values for avocado as compared to other compatible food elements for any given biomarker and/or body datum. For example, tempeh may contain a high compatibility index value for a dietary state such as vegan diet but a low compatibility index value for a dietary state such as ketogenic. Tables contained within food element compatibility index value database may include other foods including for example, chestnuts, coffee, cantaloupe melon, pistachios, arugula, bamboo shoots, beet greens, broccoli, burdock root, Italian artichoke, asparagus, beet, bok choy, Brussel sprouts, cabbage, celery (not picture). Persons skilled in the art upon reviewing the entirety of this disclosure, will be aware of various forms which may be suitable for use as compatibility index value database consistently with this disclosure.

Referring now to FIG. 8, an exemplary embodiment of Jerusalem artichoke table 700 is illustrated. For instance and without limitation, Jerusalem artichoke table 700 may contain individual compatibility index value scores for Jerusalem artichoke as compared to other biomarkers, body datums, dietary states, and food elements. For instance and without limitation, Jerusalem artichoke table 700 may contain a first column 800 containing other biomarkers, body datums, dietary states, and food elements. For instance and without limitation, Jerusalem artichoke table 700 may contain a second column 804 containing the specific compatibility index value for a Jerusalem artichoke for the particular item of comparison located in column 1 800. For instance and without limitation, Jerusalem artichoke table 700 may contain a first nutritional biomarker 808 and a compatibility index value 812 for a Jerusalem artichoke linked to first nutritional biomarker 808. For instance and without limitation, Jerusalem artichoke table 700 may contain a first body datum 816 and a compatibility index value 820 for a Jerusalem artichoke linked to first body datum 816. For instance and without limitation, Jerusalem artichoke table 700 may contain a first dietary state 824 and a compatibility index value 828 for a Jerusalem artichoke linked to first dietary state 824. For instance and without limitation, Jerusalem artichoke table 700 may contain a first food element 832 and a compatibility index value 836 for a Jerusalem artichoke linked to first food element 832. In an embodiment, Jerusalem artichoke table 700 may contain n entries of nutritional biomarkers, n entries of body datums, n entries of dietary states, and n entries of food elements. In an embodiment, each food element may contain a table listing compatibilities of each food element to each item contained within column 1 to compatibility index values contained within column 2 as described above in reference to FIG. 7.

Figure 9:
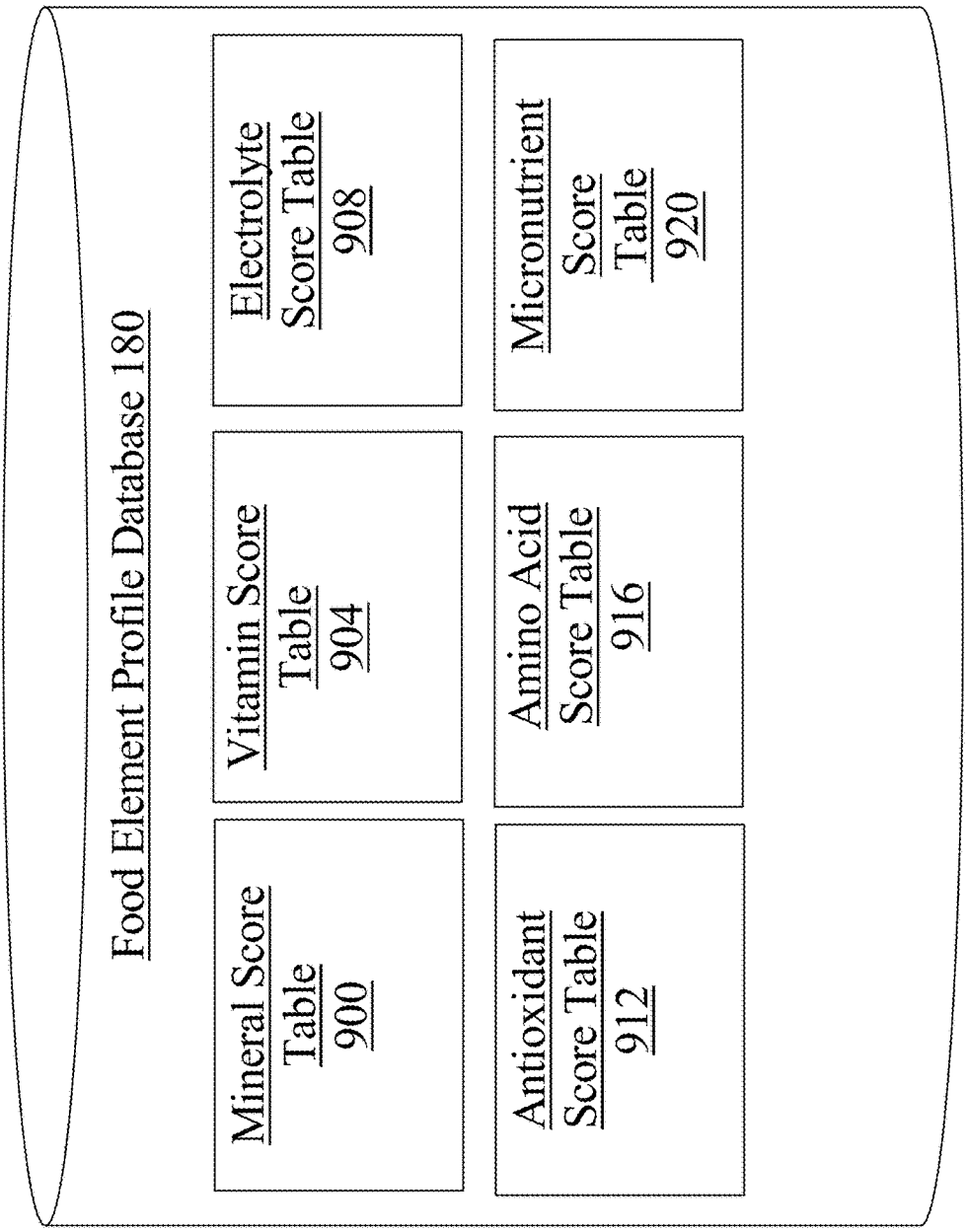
FIG. 9 is a block diagram illustrating an exemplary embodiment of a food element profile database.

Referring now to FIG. 9, an exemplary embodiment of food element profile database 172 is illustrated. Food element profile database 172 may include any data structure for ordered storage and retrieval of data, which may be implemented as a hardware or software module, and which may be implemented as any database structure suitable for use as body database 124. Food element profile database 172 may contain information containing nutrient density information about a particular food element. Data contained within food element profile database 172 may be utilized to calculate food element compatibility index value and when generating vibrant compatibility plan 192t. One or more tables contained within food element profile database 172 may include for instance mineral score table 900; mineral score table 900 may include information describing minerals contained within a particular food element. For example, mineral score table 900 may include minerals such as iron and calcium contained within a particular food element such as a banana or minerals contained within multiple food elements such as for example orange cantaloupe melon, chicken, and black lentils. One or more tables contained within food element profile database 172 may include for instance, vitamin score table 904; vitamin score table 904 may include information describing vitamins contained within a particular food element. For example, vitamin score table 904 may include vitamins such as Vitamin C, Vitamin E, and Vitamin D contained within one or more food elements such as blackstrap molasses, buckwheat, and oatmeal. One or more tables contained within food element profile database 172 may include for instance, electrolyte score table 908; electrolyte score table may include information describing electrolytes contained within a particular food element. For example, electrolyte score table 908 may include information describing electrolyte quantities such as potassium, and sodium contained within a food element such as lamb or walnuts. One or more tables contained within food element profile database 172 may include for instance, antioxidant score table 912; antioxidant score table 912 may include information describing antioxidants contained within a particular food element and/or plurality of food elements. For example, antioxidant table 912 may include information describing antioxidants that may aid in slowing oxidation or electron transfer such as for example cranberries, blueberries, grapes, raspberry, elderberry, black currants, pomegranates, plums and the like. One or more tables contained within food element profile database 172 may include for instance, amino acid score table 916; amino acid score table 916 may include information describing amino acids contained within a particular food element. For example, amino acid score table 916 may include information describing amino acids contained within a particular food element including for example amino acids such as valine, alanine, arginine, glutamine, lysine, aspartic acid, glutamic acid and the like. For example, amino acid score table 916 may include information describing quantities of amino acids such as valine and leucine contained within white turkey or quantities of lysine and aspartic acid contained within tofu. One or more tables contained within food element profile database 172 may include for instance, micronutrient score table 920; micronutrient score table 920 may include information describing quantities of micronutrients contained within a particular food element. For example, micronutrient score table 920 may include information describing quantities of folate and iodine contained within a particular food element. Information contained within food element profile database 172 may include other score tables including for example, metabolites, fatty acids, fat content, saturated fat content, protein content, carbohydrate content, (not pictured) and the like. Persons skilled in the art upon reviewing the entirety of this disclosure, will be aware of various forms which may be suitable for use as food element profile database 172 consistently with this disclosure.

Figure 10:
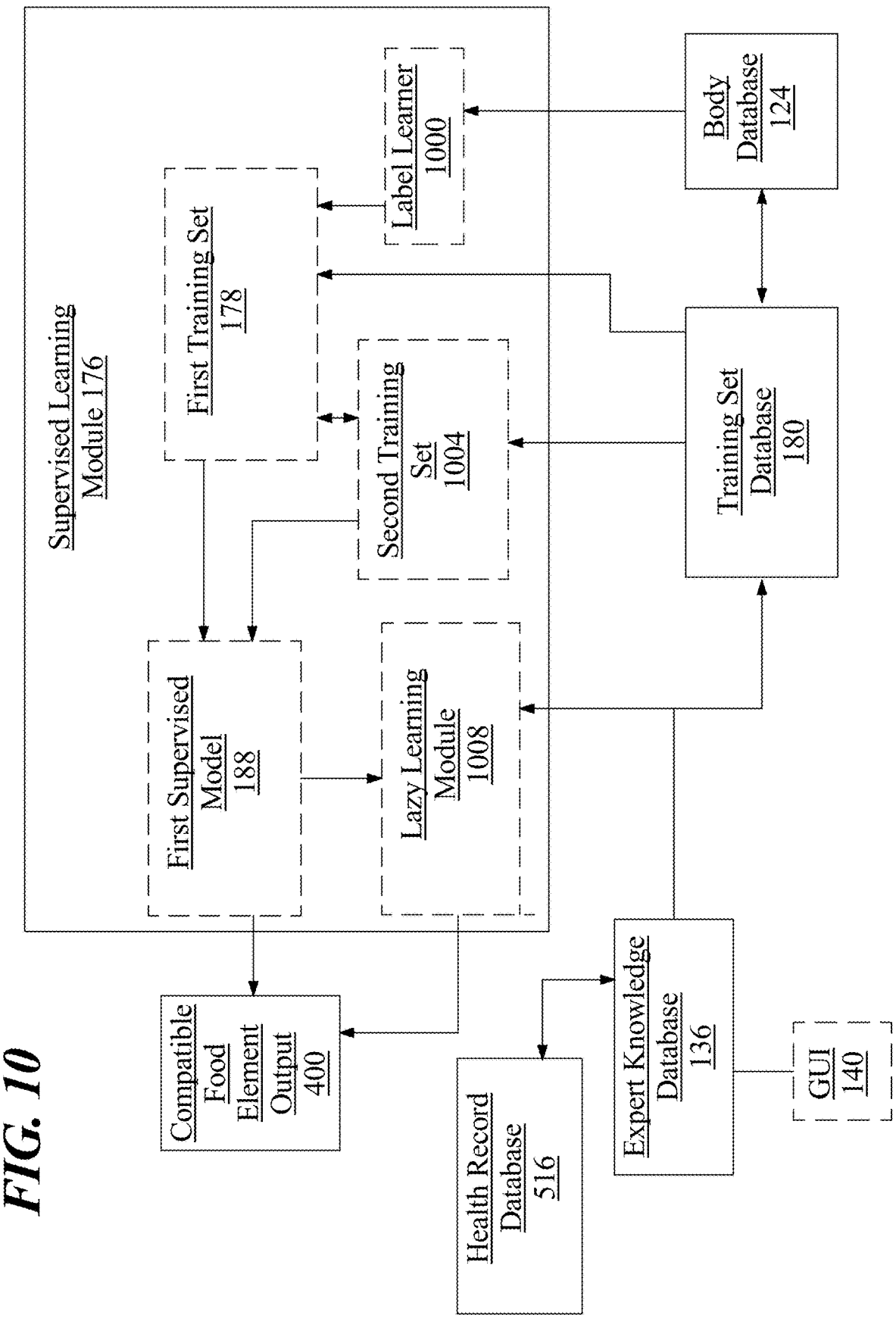
FIG. 10 is a block diagram illustrating an exemplary embodiment of a supervised learning module.

Referring now to FIG. 10, an exemplary embodiment of supervised learning module 176 is illustrated. Supervised learning module 176 may include at least a label learner 1000 designed and configured to create at least a supervised machine learning model 188 using the at least a first training set 184 wherein the at least at supervised machine learning model 188 relates body data to compatible food elements. First training set 184 may be selected from training set database 180. Supervised learning module 176 may be configured to perform any supervised machine-learning algorithm as described above in reference to FIG. 1. This may include for example, support vector machines, linear regression, logistic regression, naïve Bayes, linear discriminant analysis, decision trees, k-nearest neighbor algorithm, neural networks, and similarity learning. Supervised machine-learning module may generate a first supervised machine learning model 188 which may be utilized to generate compatible food element output 400. In an embodiment, first training set 184 may include the at least a correlated dataset. First training set 184 may be selected by categorizing the at least a user body datum to contain at least a physiological label and select at least a first training set 184 as a function of the at least a physiological label. In an embodiment, training sets contained within training set database 180 may be organized and categorized by groupings of physiological labels as described in more detail below in reference to FIG. 11.

With continued reference to FIG. 10, supervised learning module 176 may include at least a label learner 1000 which may include any hardware or software module. At least a label learner 1000 may select first training set 184 and/or second training set 1004 from training set database 180 and/or body database 124. In an embodiment, at least a label learner 1000 may generate different supervised models 186 to create learned associations between training sets and inputs and outputs utilized to select training sets such as correlations between body data and correlated compatible food elements. In an embodiment, at least a label learner 1000 may select datasets from body database 124 to be utilized as training sets. Datasets contained within body database 124 and/or training set database 180 may be generated based on inputs by experts and sources contained within expert knowledge database 136 and/or health record database 516 through submissions generated by experts at graphical user interface 140.

With continued reference to FIG. 10, supervised learning module 176 may generate compatible food element output 400 by executing a lazy learning module 1008 as a function of a user body datum and a compatible food element output 400. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover a "first guess" at an antidote associated with at least a user input datum, using at least a training set. As a non-limiting example, an initial heuristic may include a ranking of compatible food elements according to relation to a test type of at least a user body datum, one or more categories of body data identified in test type of at least a composition datum 108, and/or one or more values detected in at least a user composition datum 108 sample; ranking may include, without limitation, ranking according to significance scores of associations between elements of body data and compatible food elements, for instance as calculated as described above. Heuristic may include selecting some number of highest-ranking associations and/or compatible food elements. Lazy learning module 1008 may alternatively or additionally implement any suitable "lazy learning" algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate antidotes as described in this disclosure, including without limitation lazy learning applications of machine-learning algorithms as described in further detail below.

Figure 11:
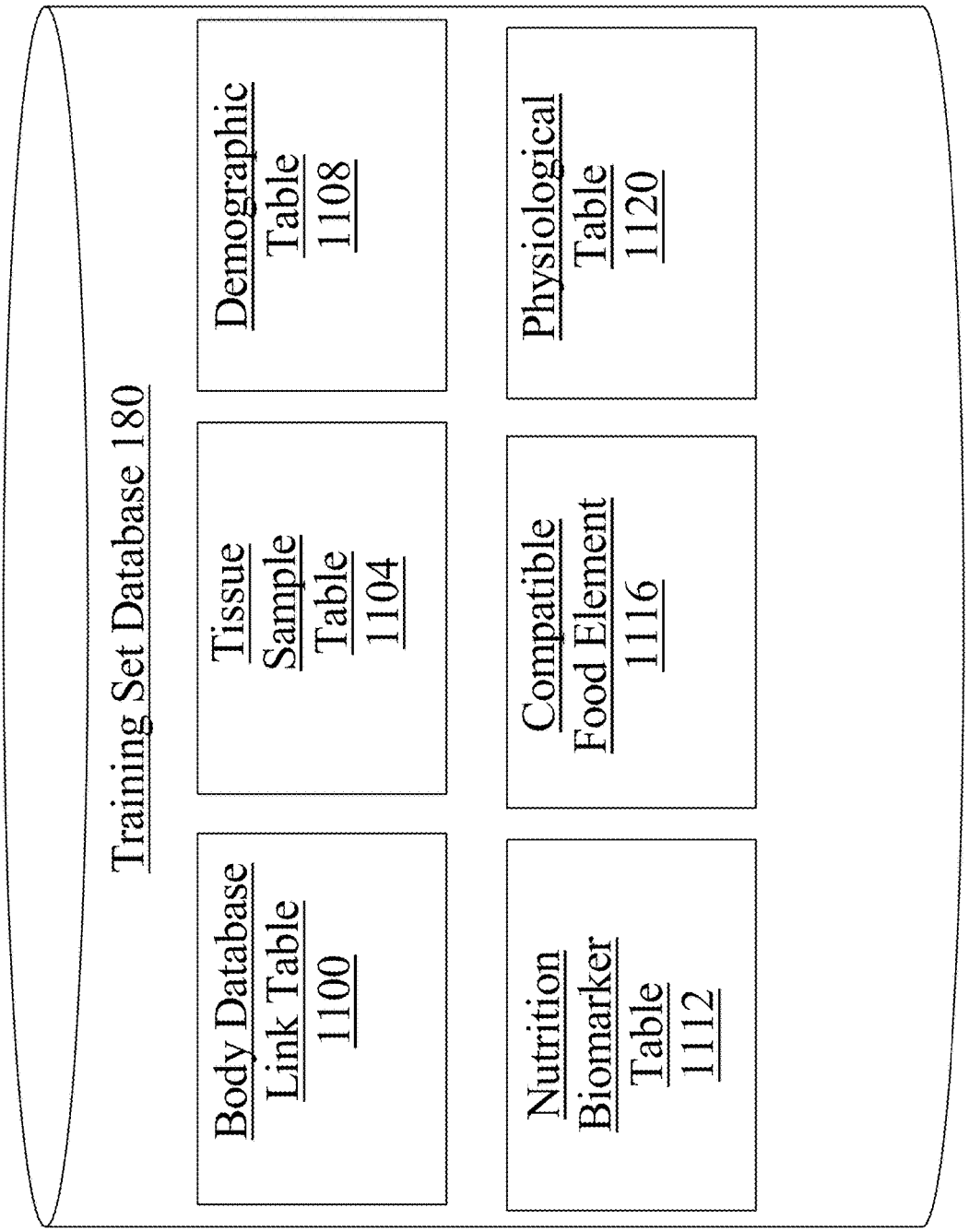
FIG. 11 is a block diagram illustrating an exemplary embodiment of a training set database.

Referring now to FIG. 11, an exemplary embodiment of training set database 180 is illustrated. Training set database 180 may include any data structure for ordered storage and retrieval of data, which may be implemented as a hardware or software module, and which may be implemented as any database structure suitable for use as body database 124. For instance and without limitation, one or more database tables contained within training set database 180 may include body database link table 1100; body database link table 1100 may contain information linking datasets contained within body database. For example, dataset contained within body database may also be contained within training set database 180 which may be linked through body database link table 1100. In yet another non-limiting example, body database link table 1100 may contain information linking datasets contained within body database to datasets contained within training set database 180, such as when dataset and training set may include data sourced from the same user or same cohort of users. For instance and without limitation, one or more database tables contained within training set database 180 may include tissue sample table 1104; tissue sample table 1104 may contain training sets containing tissue samples that may contain one or more nutritional biomarkers which may be correlated to one or more compatible food element outputs. Tissue sample table 1104 may include tissue samples such as blood, cerebrospinal fluid, urine, blood plasma, synovial fluid, amniotic fluid, lymph, tears, saliva, semen, aqueous humor, vaginal lubrication, bile, mucus, vitreous body, gastric acid, which may be correlated to a compatible food element output. For instance and without limitation, one or more database tables contained within training set database 180 may include demographic table 1108; demographic table 1108 may contain training sets containing demographics that may contain body data and one or more demographics correlated to one or more compatible food element outputs. Demographics may include residence location, geographical area where a subject may live, age, race, ethnicity, gender, marital status, income, education, employment and the like. For instance and without limitation, one or more database tables contained within training set database 180 may include nutrition biomarker table 1112; nutrition biomarker table 1112 may include one or more nutrition biomarkers correlated to one or more compatible food elements. For example, a nutrition biomarker contained within a training set may contain a biomarker such as candida overgrowth in the gastrointestinal tract correlated to a compatible food such as spinach. For instance and without limitation, one or more database tables contained within training set database 180 may include compatible food element table 1116; compatible food element table 116 may include compatible food elements correlated to other compatible food elements. For example, compatible food element table 1116 may include a first compatible food element correlated to a second compatible food element. For instance and without limitation, one or more database tables contained within training set database 180 may include physiological table 1120; physiological table 1120 may include one or more physiological labels correlated to one or more compatible food elements. For example, physiological table 1120 may include a physiological label such as neurological correlated to one more compatible food elements containing B Vitamins such as buckwheat, oats, amaranth, and barley. Persons skilled in the art upon reviewing the entirety of this disclosure, will be aware of various forms which may be suitable for use as training set database 180 consistently with this disclosure.

Figure 12:
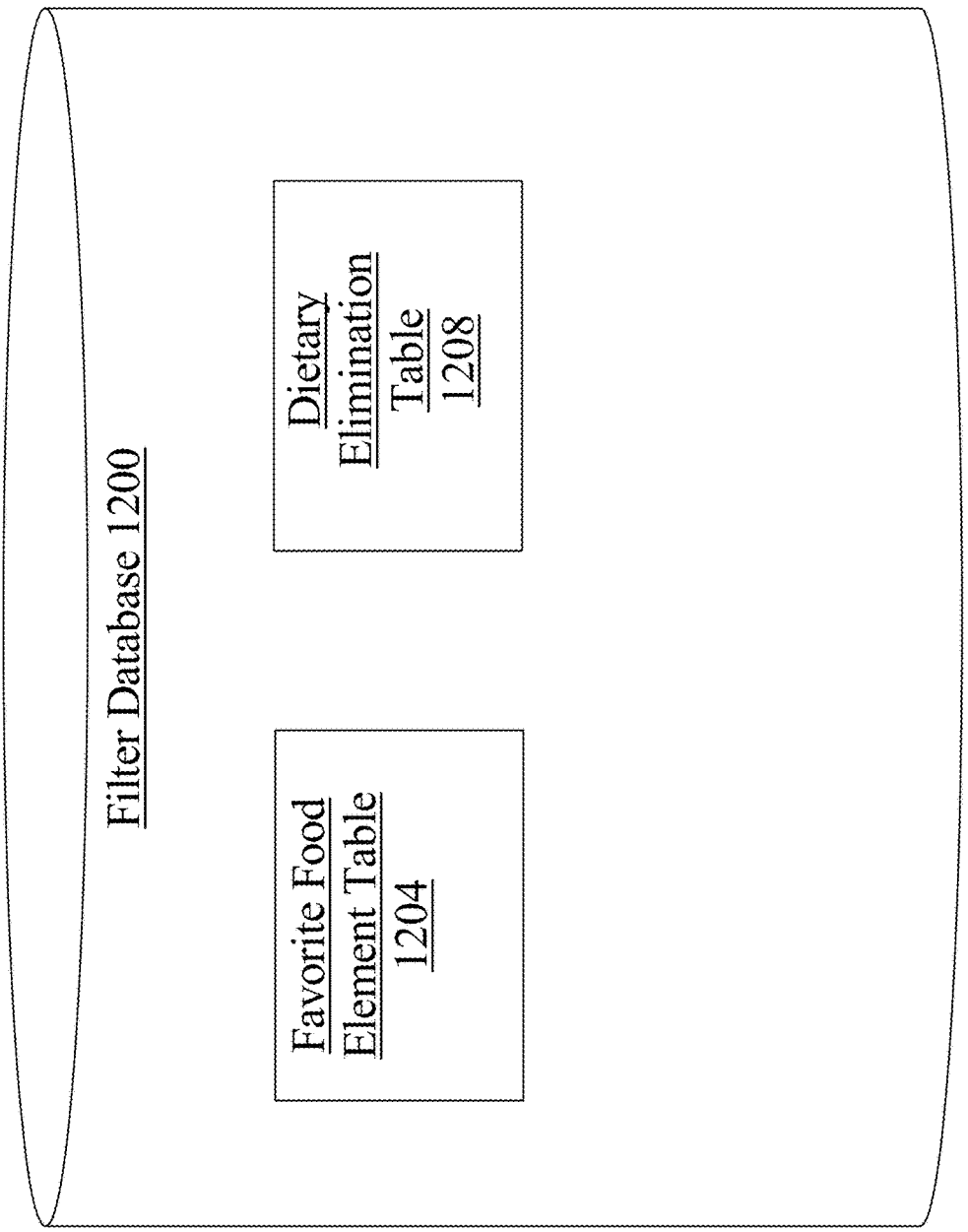
FIG. 12 is a block diagram illustrating an exemplary embodiment of a filter database.

Referring now to FIG. 12, an exemplary embodiment of filter database 1200 is illustrated. Filter database 1200 may include any data structure for ordered storage and retrieval of data, which may be implemented as a hardware or software module, and which may be implemented as any database structure suitable for use as body database 124. Filter database 1200 may include information input by user regarding user's favorite food elements and dietary restrictions. Filter database 1200 may be consulted by at least a server 104 when generating at least a vibrant compatible plan to filter off compatible food elements that may not match a user's food and eating preferences. One or more tables contained within filter database 1200 may include favorite food element table 1204; favorite food element table 1204 may include a user's preference for favorite food elements. For example, favorite food element table 1204 may include the top ten food elements that a user consumes on a weekly basis for instance. One or more tables contained within filter database 1200 may include dietary elimination table 1208; dietary elimination table 1208 may include information pertaining to a particular food element or food group that a user may need to eliminate due to a user's own personal preference to not consume a particular food element for ethical or moral reasons or due to an allergy such as an anaphylactic allergy to a food element such as tree nuts or dairy products. Persons skilled in the art upon reviewing the entirety of this disclosure, will be aware of various forms which may be suitable for use as filter database consistently with this disclosure.

Figure 13:
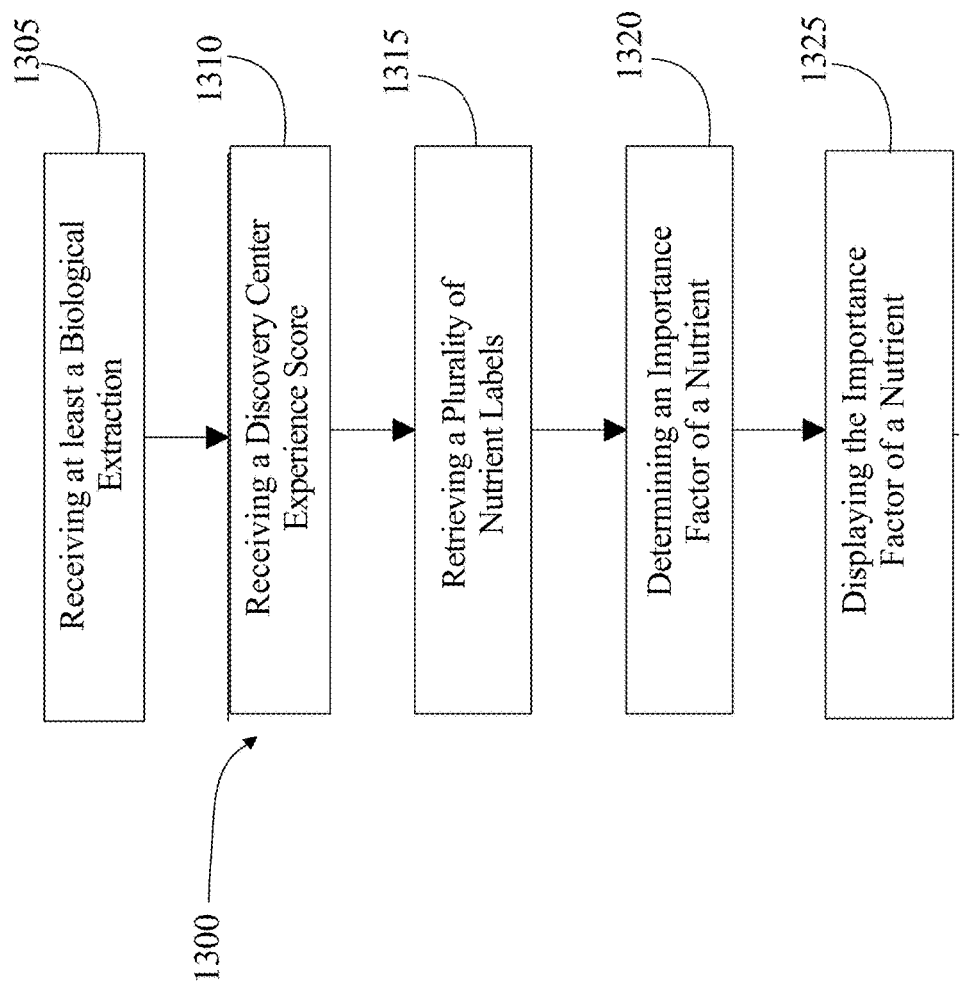
FIG. 13 is a process flow diagram illustrating an exemplary embodiment of a method for optimizing nutrition and health.

Referring now to FIG. 13, an exemplary embodiment of a method 1300 of optimizing nutrition and health is illustrated. At step 1305 at least a computing device 102 received at least a biological extraction 114 from a user. This may be implemented, for instance, as described above in reference to FIGS. 1-12. At least a biological extraction 114 may include a genetic sample, an endocrinal sample and the like. Biological extraction 114 may be labeled to a category, such as a body system, and may be measured. As a further non-limiting example, the at least a biological extraction may include a signal from at least a sensor configured to detect physiological data of a user and recording the at least a biological extraction as a function of the signal.

With continued reference to FIG. 13, at step 1310 at least a computing device 102 receives a discovery center experience score 118 related to a user. This may be implemented, for instance, as described above in reference to FIGS. 1-12. The discovery center experience score 118 may be based on one or more discovery center experiences and may be ranked. The discovery center experience score 118 may include a biological extraction of a user corresponding to a discovery center experience and the discovery center experience may include a set of simulated data generated at an online platform. The discovery center experience describes health experiences to optimize a user's health such as gut health optimization.

With continued reference to FIG. 13, at step 1315 at least a computing device 102 retrieves a plurality of nutrient labels describing a plurality of nutrients. This may be implemented, for instance, as described above in reference to FIGS. 1-12. In an embodiment, apparatus 138 may be configured to retrieve a plurality of nutrient labels 126 describing a plurality of nutrients. For example, a plurality of nutrient labels 126 may include data related to various nutrients such as the level of Vitamin C in an orange.

With continued reference to FIG. 13, at step 1320 at least a computing device determines, as a function of the discovery center experience score 118 and biological extraction 114, an importance factor of a nutrient 130. This may be implemented, for instance, as described above in reference to FIGS. 1-12. The importance factor of a nutrient may be scored and may include the importance of nutrients based on the impact of a user's biochemical process. A proprietary calculation to establish importance of nutrients/toxins based on impact (positive or negative) on human physiology, storage in the body, number of physiological functions and biochemical processes may be performed. In an embodiment, computing device 102 may utilize the discovery center experience score 118 and user biological extraction 114 data to influence the nutrient importance factor score 130. For example, if it is determined that a user's bone health is poor, then the nutrient calcium will be more important to user than a nutrient like folate, which is used for heart health.

With continued reference to FIG. 13, at step 1325 at least a computing device displays the importance factor of a nutrient 130 of a plurality of nutrients to a user. This may be implemented, for instance, as described above in reference to FIGS. 1-12. In an embodiment, apparatus 138 may be configured to display the importance factor of a nutrient of a plurality of nutrients to a user on a user display 134.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 14:
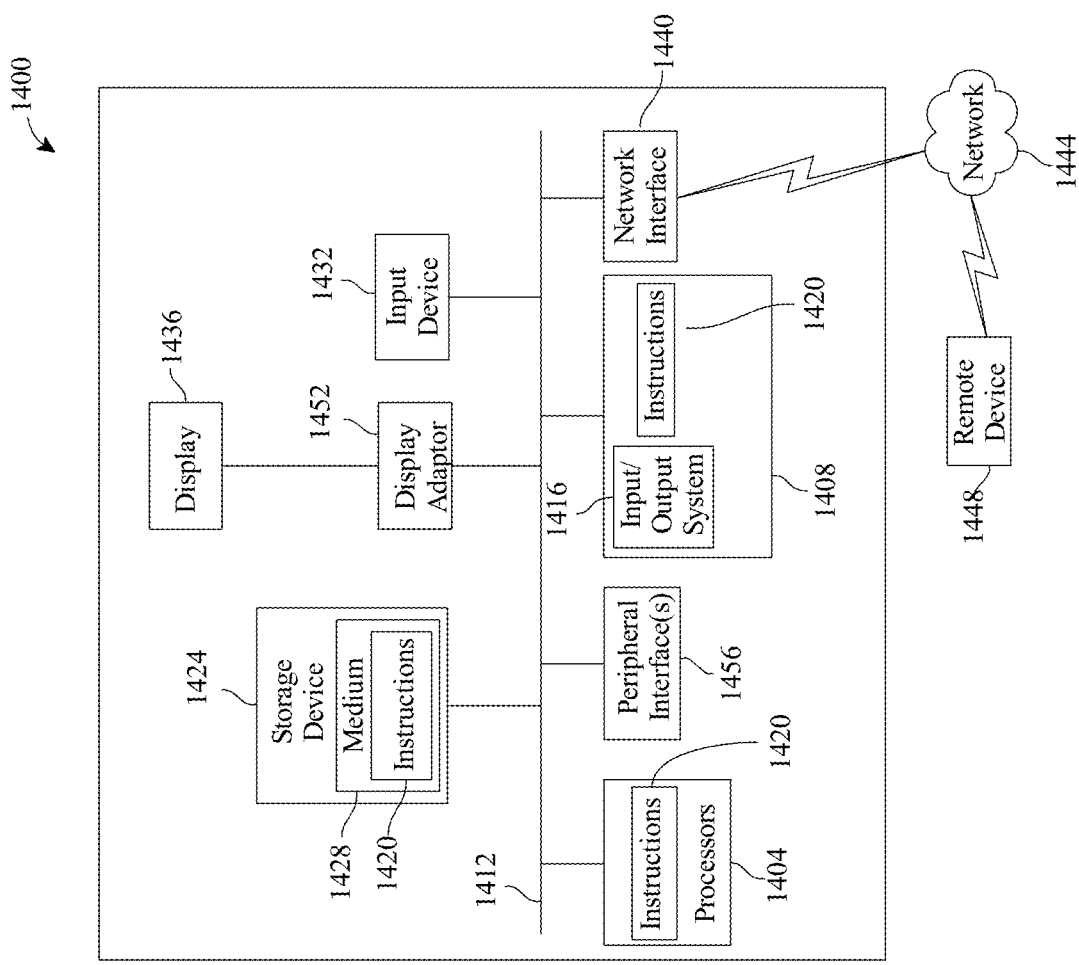
FIG. 14 is a block diagram of a computing system that can be used to implement any one or more of the methodologies disclosed herein and any one or more portions thereof.

FIG. 14 shows a diagrammatic representation of one embodiment of a computing device in the exemplary form of a computer system 1400 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1400 includes a processor 1404 and a memory 1408 that communicate with each other, and with other components, via a bus 1412. Bus 1412 may include any of several types of bus structures including, but not limited to, a memory bus, a memory controller, a peripheral bus, a local bus, and any combinations thereof, using any of a variety of bus architectures.

Memory 1408 may include various components (e.g., machine-readable media) including, but not limited to, a random access memory component, a read only component, and any combinations thereof. In one example, a basic input/output system 1416 (BIOS), including basic routines that help to transfer information between elements within computer system 1400, such as during start-up, may be stored in memory 1408. Memory 1408 may also include (e.g., stored on one or more machine-readable media) instructions (e.g., software) 1420 embodying any one or more of the aspects and/or methodologies of the present disclosure. In another example, memory 1408 may further include any number of program modules including, but not limited to, an operating system, one or more application programs, other program modules, program data, and any combinations thereof.

Computer system 1400 may also include a storage device 1424. Examples of a storage device (e.g., storage device 1424) include, but are not limited to, a hard disk drive, a magnetic disk drive, an optical disc drive in combination with an optical medium, a solid-state memory device, and any combinations thereof. Storage device 1424 may be connected to bus 1412 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1424 (or one or more components thereof) may be removably interfaced with computer system 1400 (e.g., via an external port connector (not shown)). Particularly, storage device 1424 and an associated machine-readable medium 1428 may provide nonvolatile and/or volatile storage of machine-readable instructions, data structures, program modules, and/or other data for computer system 1400. In one example, software 1420 may reside, completely or partially, within machine-readable medium 1428. In another example, software 1420 may reside, completely or partially, within processor 1404.

Computer system 1400 may also include an input device 1432. In one example, a user of computer system 1400 may enter commands and/or other information into computer system 1400 via input device 1432. Examples of an input device 1432 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1432 may be interfaced to bus 1412 via any of a variety of interfaces (not shown) including, but not limited to, a serial interface, a parallel interface, a game port, a USB interface, a FIREWIRE interface, a direct interface to bus 1412, and any combinations thereof. Input device 1432 may include a touch screen interface that may be a part of or separate from display 1436, discussed further below. Input device 1432 may be utilized as a user selection device for selecting one or more graphical representations in a graphical interface as described above.

A user may also input commands and/or other information to computer system 1400 via storage device 1424 (e.g., a removable disk drive, a flash drive, etc.) and/or network interface device 1440. A network interface device, such as network interface device 1440, may be utilized for connecting computer system 1400 to one or more of a variety of networks, such as network 1444, and one or more remote devices 1448 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1444, may employ a wired and/or a wireless mode of communication. In general, any network topology may be used. Information (e.g., data, software 1420, etc.) may be communicated to and/or from computer system 1400 via network interface device 1440.

Computer system 1400 may further include a video display adapter 1452 for communicating a displayable image to a display device, such as display device 1436. Examples of a display device include, but are not limited to, a liquid crystal display (LCD), a cathode ray tube (CRT), a plasma display, a light emitting diode (LED) display, and any combinations thereof. Display adapter 1452 and display device 1436 may be utilized in combination with processor 1404 to provide graphical representations of aspects of the present disclosure. In addition to a display device, computer system 1400 may include one or more other peripheral output devices including, but not limited to, an audio speaker, a printer, and any combinations thereof. Such peripheral output devices may be connected to bus 1412 via a peripheral interface 1456. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for optimizing nutrition and health, comprising:
    at least a processor and a memory communicatively connected to the at least a processor, the memory containing instructions configuring the at least a processor to:
    receive at least a biological extraction from a user;
    display, using a user display device, a discovery center experience, wherein the discovery center experience is an online platform;
    extract data from a discovery center experience, wherein the discovery center experience comprises a set of generated simulated data;
    receive a discovery center experience score related to the user as a function of the extracted data;
    retrieve a plurality of nutrient labels describing a plurality of nutrients;
    determine, as a function of the discovery center experience score and biological extraction, an importance factor of a nutrient of the plurality of nutrients, wherein determining the importance factor of a nutrient further comprises:
        receiving discovery center experience score training data correlating biological extraction data elements to a discover center experience data elements;
        training a machine learning model as a function of the biological extraction data; and
        outputting the importance factor of a nutrient as a function of the machine learning model; and
    display the importance factor to the user.

2. The apparatus of claim 1, wherein the discovery center experience score is ranked.

3. The apparatus of claim 1, wherein the importance factor of a nutrient is scored.

4. The apparatus of claim 1, wherein the discovery center experience score is based on at least a discovery center experience.

5. The apparatus of claim 4, wherein the at least a discovery center experience comprises a microbiome test.

6. The apparatus of claim 4, wherein the at least a discovery center experience further comprises a set of simulated data generated at a discovery center.

7. The apparatus of claim 4, wherein the at least a discovery center experience describes health experiences to optimize a user's health.

8. The apparatus of claim 4, wherein the discovery center experience comprises describes health experiences to optimize gut health.

9. The apparatus of claim 1, wherein the importance factor of a nutrient includes a factor indicating an importance of nutrients based on an impact of a user's biochemical process.

10. A method of using a computing device for optimizing nutrition and health comprising:
    receiving at least a biological extraction from a user;
    displaying, using a user display device, a discovery center experience, wherein the discovery center experience is an online platform;
    extracting data from a discovery center experience, wherein the discovery center experience comprises a set of generated simulated data;
    receiving a discovery center experience score related to a user as a function of the extracted data;
    retrieving a plurality of nutrient labels describing a plurality of nutrients;
    determining, as a function of the discovery center experience score and biological extraction, an importance factor of a nutrient, wherein determining the importance factor of a nutrient further comprises:
        receiving discovery center experience score training data correlating biological extraction data elements to a discover center experience data elements;
        training a machine learning model as a function of the biological extraction data; and
        outputting the importance factor of a nutrient as a function of the machine learning model; and
    displaying the importance factor of a nutrient of a plurality of nutrients to a user.

11. The method of claim 10, wherein the discovery center experience score is ranked.

12. The method of claim 10, wherein the importance factor of a nutrient is scored.

13. The method of claim 10, wherein the discovery center experience score is based on one or more discovery center experiences.

14. The method of claim 13, wherein the discovery center experience comprises a microbiome test.

15. The method of claim 13, wherein the discovery center experience comprises a set of simulated data generated at an online platform.

16. The method of claim 13, wherein the discovery center experience describes health experiences to optimize a user's health.

17. The method of claim 13, wherein the discovery center experience comprises gut health optimization.

18. The method of claim 10, wherein the importance factor of a nutrient includes the importance of nutrients based on an impact of a user's biochemical process.

* * * * *